United States Patent
Blagg et al.

(10) Patent No.: US 9,056,104 B2
(45) Date of Patent: Jun. 16, 2015

(54) DYNAMIC INHIBITORS OF HEAT SHOCK PROTEIN 90

(75) Inventors: Brian S. J. Blagg, Lawrence, KS (US); Bhaskar Reddy Kusuma, Lawrence, KS (US)

(73) Assignee: THE UNIVERSITY OF KANSAS, Lawrence, KS (US)

( * ) Notice: Subject to any disclaimer, the term of this patent is extended or adjusted under 35 U.S.C. 154(b) by 21 days.

(21) Appl. No.: 13/473,046

(22) Filed: May 16, 2012

(65) Prior Publication Data

US 2012/0309702 A1    Dec. 6, 2012

Related U.S. Application Data

(60) Provisional application No. 61/488,321, filed on May 20, 2011.

(51) Int. Cl.
*A61K 31/4545* (2006.01)
*A61K 31/352* (2006.01)
*A61K 31/7048* (2006.01)

(52) U.S. Cl.
CPC ........... *A61K 31/4545* (2013.01); *A61K 31/352* (2013.01); *A61K 31/7048* (2013.01)

(58) Field of Classification Search
None
See application file for complete search history.

(56) References Cited

U.S. PATENT DOCUMENTS

2011/0082098 A1    4/2011   Calvet et al.

FOREIGN PATENT DOCUMENTS

| WO | 00/53169 A2 | 9/2000 |
| WO | WO 2010096650 A1 * | 8/2010 |

OTHER PUBLICATIONS

Burlison et al. Organic Letters 2006 vol. 8, No. 21, 4855-4858.*
Lu et al. Bioorganic & Medicinal Chemistry 17 (2009) 1709-1715.*
Kusuma et al. J Med Chem Sep. 22, 2011; 54(18): 6234-6253.*
International Search Report dated Sep. 26, 2012 as received in application No. PCT/US2012/038105.
Written Opinion of the International Searching Authority dated Sep. 26, 2012 as received in application No. PCT/US2012/038105.

* cited by examiner

*Primary Examiner* — Layla Bland
(74) *Attorney, Agent, or Firm* — Parker Highlander PLLC

(57) ABSTRACT

An inhibitor of heat shock protein 90 (HSP90) can include a coumermycin A1 analog having a structure that inhibits HSP90 greater than coumermycin A1. That is, the coumermycin A1 analog is not coumermycin A1. The coumermycin A1 analog can have an antiproliferative biological activity, which can be superior to coumermycin A1. The activity can include the coumermycin A1 analog inhibiting a C-terminus of HSP90.

27 Claims, 14 Drawing Sheets

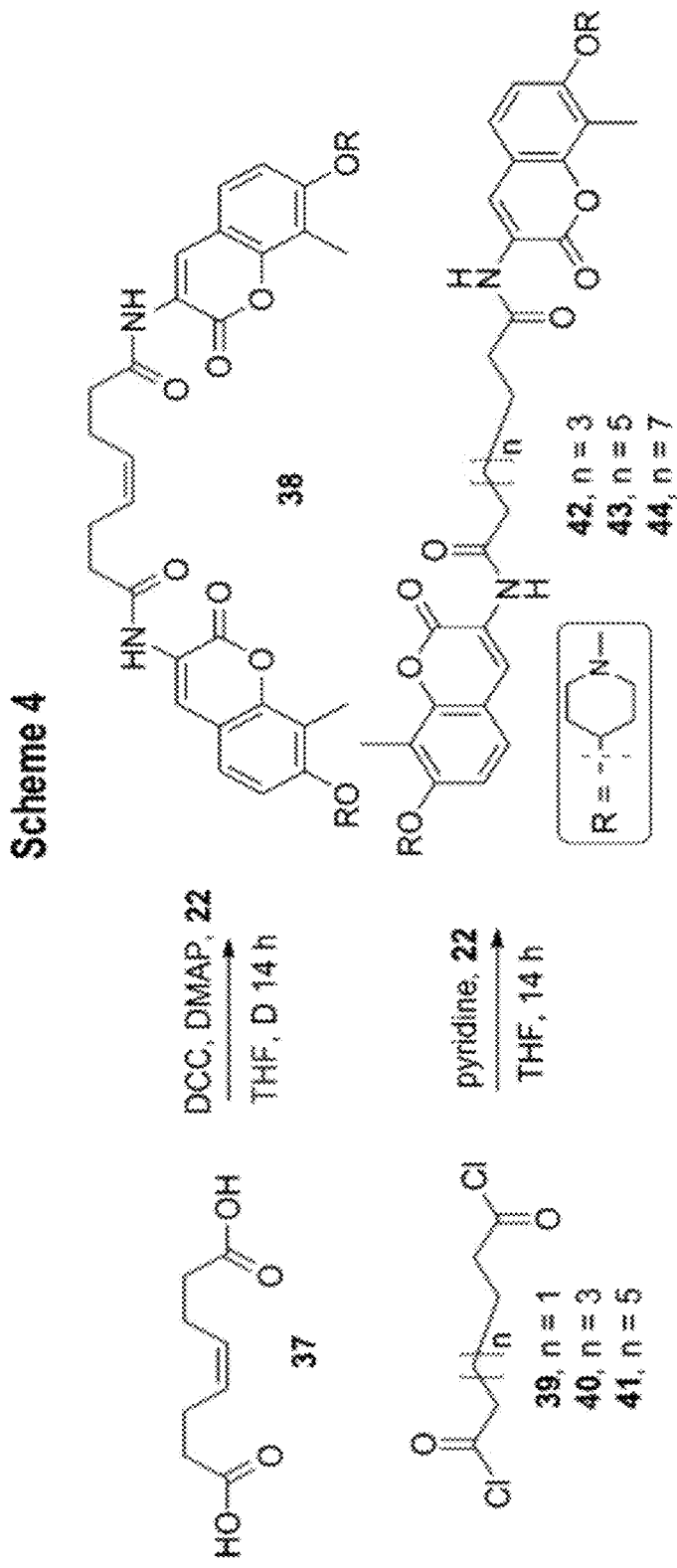

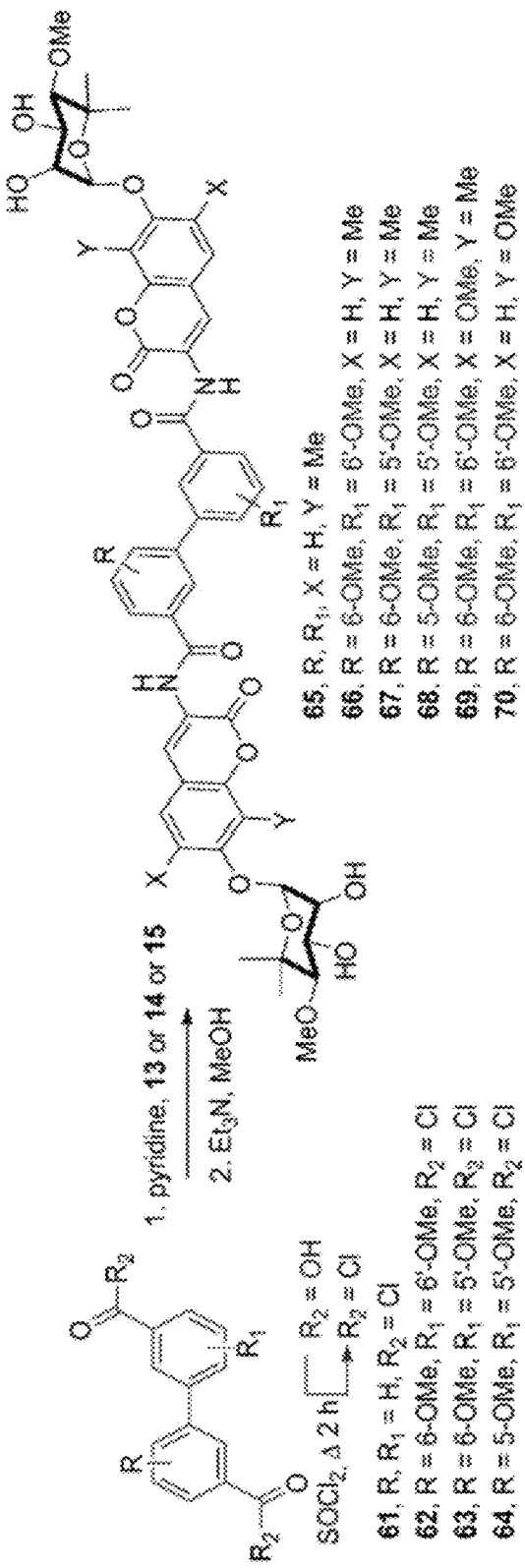
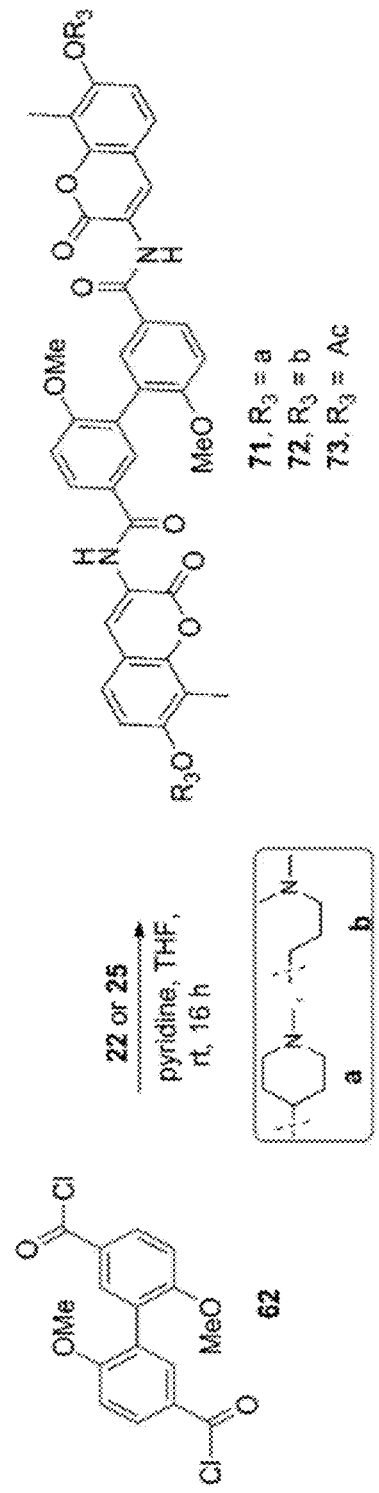
Fig. 6

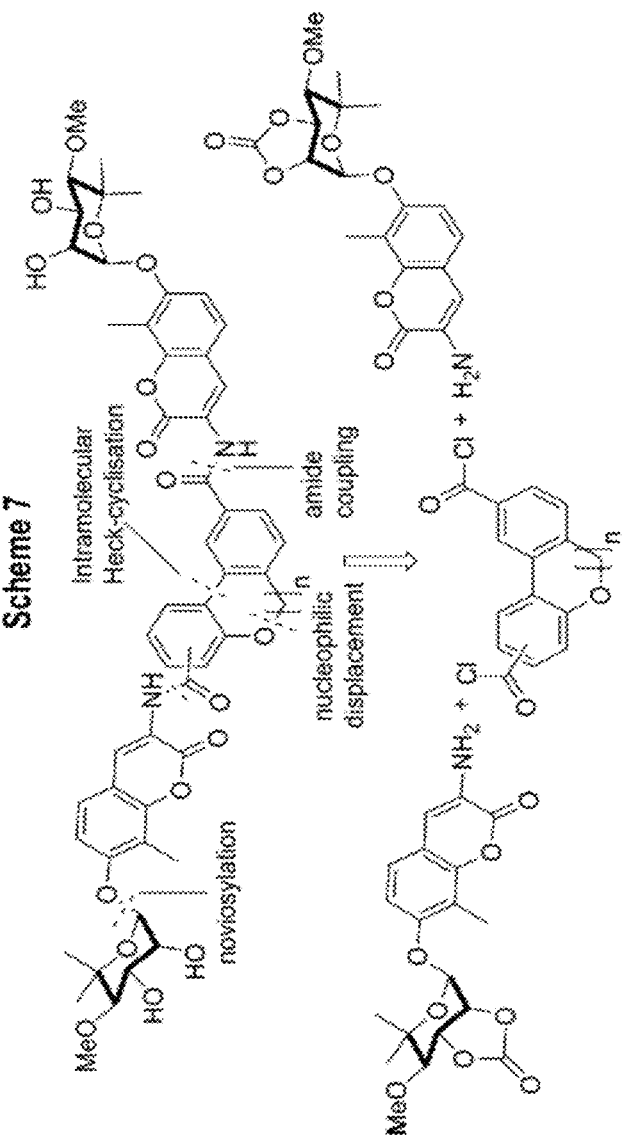
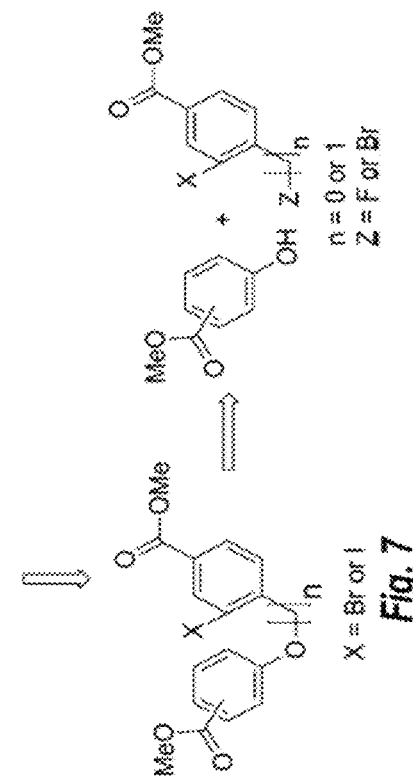
Fig. 7

DYNAMIC INHIBITORS OF HEAT SHOCK PROTEIN 90

CROSS-REFERENCE TO RELATED APPLICATION

This patent application claims the benefit of U.S. Provisional Application Ser. No. 61/488,321, filed on May 20, 2011, which provisional application is incorporated herein by specific reference in its entirety.

GOVERNMENT RIGHTS

This invention was made with government support under CA120458, T32 GM008545 awarded by the National Institutes of Health. The government has certain rights in the invention.

BACKGROUND

Heat shock protein 90 (HSP90) inhibitors exhibit promising anti-cancer properties because various proteins associated with malignant growth, including growth factors, kinases, and hormone receptors, are dependent upon the HSP90 protein folding machinery for their maturation and/or activation. See: Bishop, S. C.; Burlison, J. A.; Blagg, B. S. J. *Curr. Cancer Drug Tar.* 2007, 7, 369; Donnelly, A.; Blagg, B. S. J. *Curr. Med. Chem.* 2008, 15, 2702; Solit, D. B.; Chiosis, G. *Drug Discov. Today* 2008, 13, 38; and Peterson, L. B.; Blagg, B. S. J. *Future Med. Chem.* 2009, 1, 267. As a molecular chaperone, HSP90 is responsible for folding these client substrates. Consequently, inhibitors of HSP90 can disrupt multiple signaling cascades simultaneously, resulting in a combinatorial attack on numerous signaling pathways. See: Xu, W.; Neckers, L. *Clin. Cancer Res.* 2007, 13, 1625; and Zhang, H.; Burrows, F. *J. Mol. Med.* 2004, 82, 488.

SUMMARY

In one embodiment, an inhibitor of heat shock protein 90 (HSP90) can include a coumermycin A1 analog having a structure that inhibits HSP90 greater than coumermycin A1. That is, the coumermycin A1 analog is not coumermycin A1. The coumermycin A1 analog can have an antiproliferative biological activity, which can be superior to coumermycin A1. The activity can include the coumermycin A1 analog inhibiting a C-terminus of HSP90.

In one embodiment, the coumermycin A1 analog can be synthesized by a scheme described herein.

In one embodiment, the coumermycin A1 analog can be used in a method for inhibiting HSP90. Such a method of inhibiting HSP90 can include: providing a coumermycin A1 analog as described herein; and contacting the coumermycin A1 analog with a HSP90 so as to inhibit the HSP90. The HSP90 can be located in a body, such as in a cancerous cell of a patient that has cancer. In one aspect, the HSP90 is in a breast cancer or a prostate cancer.

In one embodiment, the coumermycin A1 analog can have an HSP90 inhibiting activity that is greater than or about 10 times the activity of coumermycin A1. In one aspect, the coumermycin A1 analog can have a nanomolar HSP90 inhibiting activity. In one aspect, the coumermycin A1 analog can interact with a C-terminal dimerization domain of the HSP90. In one aspect, the coumermycin A1 analog can have an antiproliferative activity of greater than or about $IC_{50}=70$ μM. In one aspect, the coumermycin A1 analog can be administered from about 200 to about 400 nM to a subject in need thereof, such as having or being susceptible to cancer.

In one embodiment, the coumermycin A1 analog includes a 6- or 8-methoxy coumarin or a 8-methyl-6-methoxy coumarin, and has from about 2 to about 20 times increased activity compared to coumermycin A1.

In one embodiment, the coumermycin A1 analog includes a 6- or 8-alkoxy coumarin or a 8-alkyl-6-alkoxy coumarin, and has from about 2 to about 20 times increased activity compared to coumermycin A1.

In one embodiment, the coumermycin A1 analog has a structure of one of Compounds 26-36, and wherein the HSP90 inhibiting activity is about 10 to about 100 times greater than coumermycin A1.

In one embodiment, the coumermycin A1 analog has an activity that induces degradation of HSP90-dependent client proteins. In one aspect, the coumermycin A1 analog has an activity that induces degradation of Her-2, Raf, or Akt.

In one embodiment, a method of degrading a HSP90-dependent client protein can include: providing a coumermycin A1 analog as described herein; and contacting the coumermycin A1 analog with a HSP90-dependent client protein so as to degrade the client protein. In one aspect, the client protein can be Her-2, Raf, or Akt.

In one embodiment, a method of inhibiting cell proliferation can include: providing a coumermycin A1 analog as described herein; and contacting the coumermycin A1 analog with a potentially proliferative cell in a sufficient amount to inhibit proliferation of cell.

In one embodiment, a method of inhibiting cancer cell proliferation can include: providing a coumermycin A1 analog as described herein; and contacting the coumermycin A1 analog with a cancerous cell in a sufficient amount to inhibit proliferation of cancerous cell.

DESCRIPTION OF FIGURES

FIG. 4 shows Scheme 4, which can be described as synthesis of saturated- and cis-dimers.

FIG. 6 shows Scheme 6, which can be described as a synthesis of biaryl noviosylated dimers.

FIG. 7 shows Scheme 7, which can be described as retrosynthesis of 5- and 6-membered tricyclic-tether analogs.

DETAILED DESCRIPTION

Figure 1:
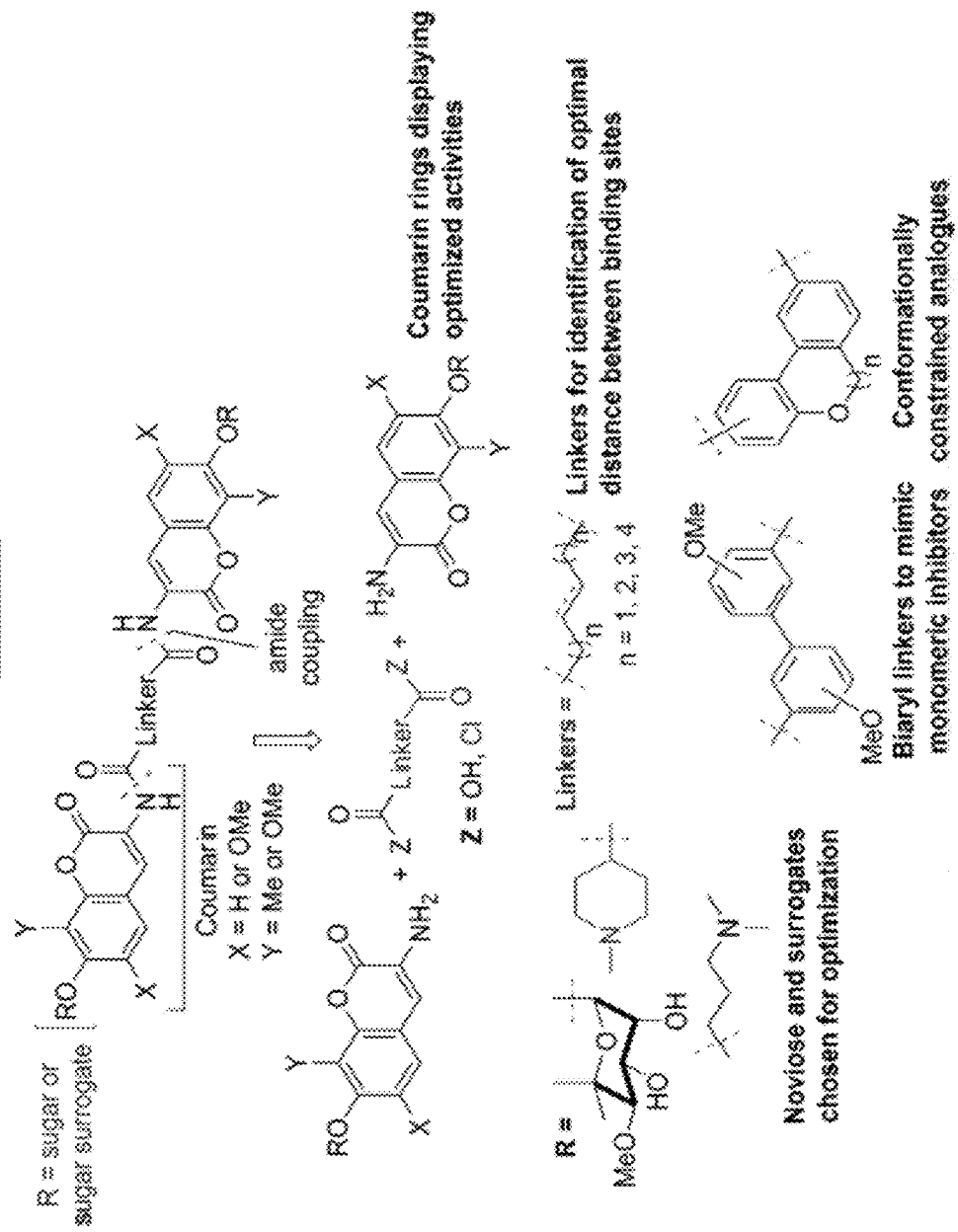
FIG. 1 shows Scheme 1, which can be described as a retrosynthesis of coumermycin A1 analogs.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to coumermycin A1 analogs that have biological activity and impact the functionality of HSP90 proteins, degrade HSP90-dependent client protein, and/or inhibit cellular proliferation. The coumermycin A1 analogs can have one or more substituents so that the analog is not coumermycin A1. The biological activity of the coumermycin A1 analog can include associating or otherwise interacting with an HSP90 in order to inhibit the HSP90 from promoting cell proliferation or facilitating cancerous growth. Also, the biological activity can lead to the degradation of HSP90-dependent client proteins such as Her-2, Raf, or Akt, which degradation can also inhibit cell proliferation or cancerous growth. By having this biological activity, the coumermycin A1 analog can be used in methods for inhibiting cell proliferation or cancerous growth.

The coumermycin A1 analogs have been evaluated against both breast cancer (e.g., SKBr3 and MCF7) and prostate cancer (e.g., PC3mm2, A549 and HT29) cell lines. The non-noviosylated coumermycin A1 analogs (e.g., without noviose sugar present in some analogs) were shown to have potent anti-proliferative activity resulting from HSP90 inhibition. These non-noviosylated coumermycin A1 analogs can be described has having a substituent or hydrogen replacing the stereochemically complex noviose sugar, where the substituent can be exemplified with piperidine rings. The coumermycin A1 analogs having the piperidine rings resulted in about a 100 fold increase in anti-proliferative activities compared to coumermycin A1 analog having the noviose sugar. These coumermycin A1 analogs can now be considered small molecule HSP90 inhibitors that have nanomolar activities.

In one embodiment, the coumermycin A1 analogs can inhibit the biological functionality of HSP90. The activity can inhibit the formation of the HSP90 homodimer. The activity can inhibit the HSP90 from binding with client proteins. Typically, HSP90 functions as a chaperone, but coumermycin A1 analogs can inhibit the function as a chaperone, possibly by interacting with one or more of the multiple small molecule binding sites of HSP90. For example, the coumermycin A1 analogs can inhibit the N-terminal nucleotide binding site, or inhibit the binding site located proximal to the C-terminal dimerization domain.

The coumermycin A1 analogs can function as HSP90 inhibitors and exhibit anti-cancer properties. In part, the inhibition activity inhibits HSP90 from interacting with proteins that are associated with malignant growth such as growth factors, kinases, and hormone receptors, which can be dependent upon the HSP90 protein folding machinery. Accordingly, the coumermycin A1 analogs can function to inhibit HSP90 from folding the client protein substrates. Thus, the coumermycin A1 analogs can disrupt multiple HSP90-related signaling cascades simultaneously and inhibit signaling pathways.

Previously novobiocin (Compound 1) was identified as the first HSP90 C-terminal inhibitor. However, novobiocin was found to be unsuitable due to its low efficacy against cancer cells (IC$_{50}$~700 μM). A dimeric compound of clorobiocin (Compound 2), which is coumermycin A1 (Compound 3), was found to have a 10-fold increase in anti-proliferative activity (IC$_{50}$=70 μM) over novobiocin. Now, coumermycin A1 analogs have been shown to have significantly higher activity that coumermycin A1.

(Compound 1)

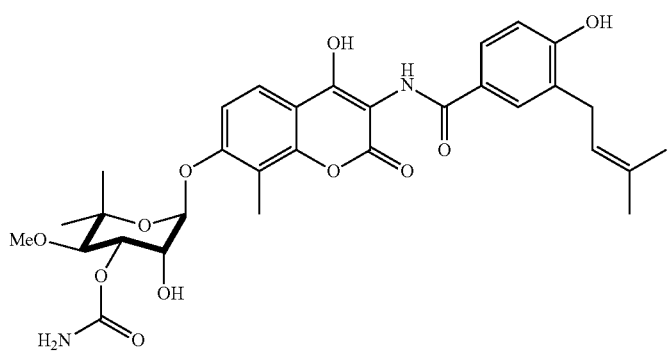

Novobiocin (Compound 2)

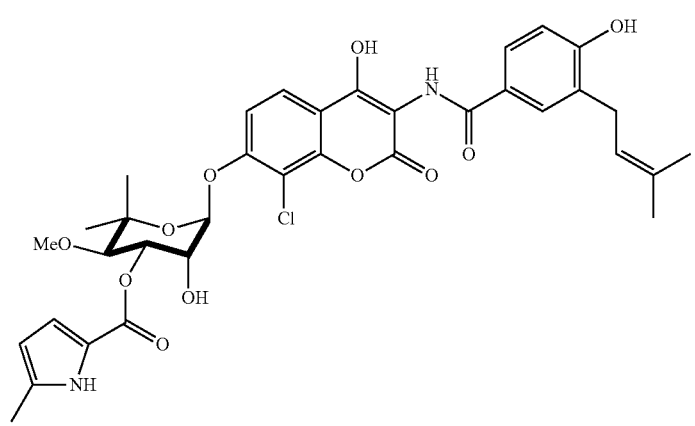

Clorobiocin (Compound 3)

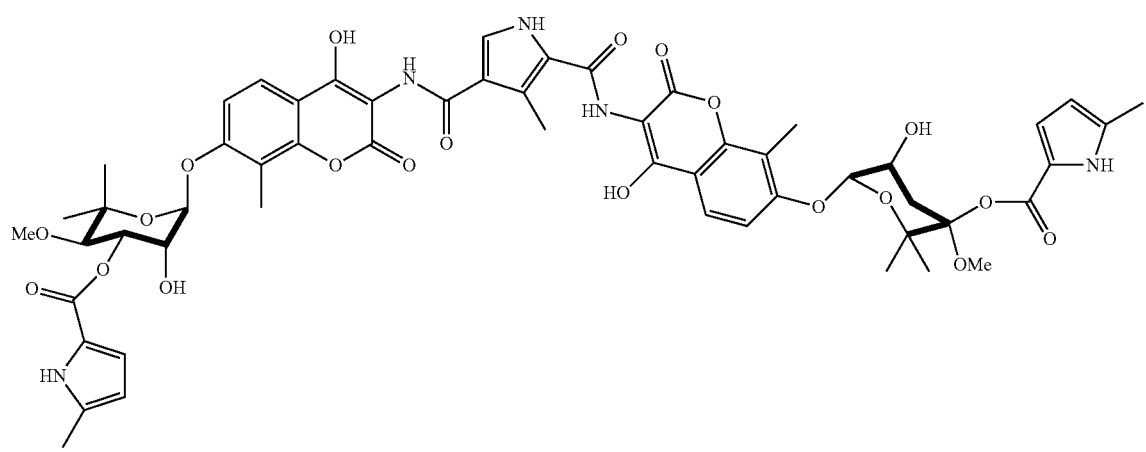

Coumermycin A1

Coumermycin A1 is a homobifunctional dimer; each monomeric unit contains a 3'-substituted noviose sugar and a 4-hydroxy-8-methylcoumarin that are connected at the 3-position of the coumarin through a 5-methylpyrrole linker. Previous coumermycin A1 analogs exchanged the pyrrole linker for an aryl, heteroaryl or olefin-containing tether that altered both the length and geometry of the linker (Burlison, J. A.; Blagg, B. S. Org. Lett. 2006, 8, 4855). Therefore, the coumermycin A1 analogs of the present invention can be devoid of having the pyrrole linker exchanged for an aryl, heteroaryl or olefin-containing tether. However, this exchange can be used when combined with other analog modifications described herein.

The coumermycin A1 analogs of the present invention can be optimized to be C-terminal inhibitors. In one aspect, the 8-methyl group is replaced with an 8-methoxy. Also, the analog can be an 8-methyl-6-methoxy coumarin. Additionally, the substituted noviose sugar can be replaced with N-methyl-4-piperidine or N,N-dimethyl ethyl amine. Also, the substituted noviose sugar of coumermycin A1 can be modified so that it is not substituted. In order to inhibit the conformationally flexible nature of the HSP90 homodimer, the 5-methylpyrrole linker of coumermycin A1 can be exchanged for bicyclic, tricyclic, and flexible tethers so that the analog is capable of binding both sites simultaneously.

The coumermycin A1 analogs can include modifications at one or more of three regions of coumermycin A: the coumarin core, the sugar, and the linker. The sugar can be replaced with N-methyl-4-piperidine and N—N-dimethyl ethyl amine, which were found to have increased anti-proliferative activities against a range of cancer cell lines. Additionally, coumermycin A1 analogs having 6- and/or 8-alkoxy substituted and 6,8-disubstituted coumarins were found to be more active than the 8-methyl coumarin. The linkers can be modified to determine the optimal distance between the monomeric binding sites and to account for the flexible nature of the chaperone. Although the alkane- and alkene-containing linkers can be used to determine the distance between these binding sites, which are located adjacent to the dimerization domain, the biaryl and tricycle containing linkers can be included in coumermycin A1 analogs.

In one embodiment, the coumermycin A1 analog has a structure of Scaffold 1, where $R^1$ or $R^2$ or $X^1$ or $X^2$ or $Y^1$ or $Y^2$ can be independently any substituent and the linker can be any linker in accordance with descriptions provided herein.

(Scaffold 1)

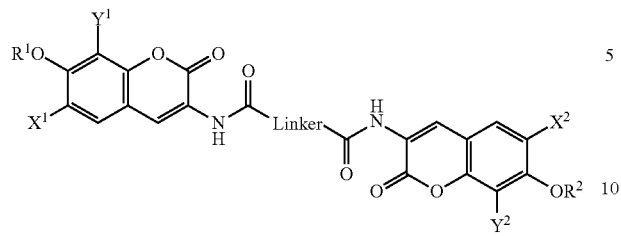

In one embodiment, $R^1$ or $R^2$ or $X^1$ or $X^2$ or $Y^1$ or $Y^2$ of Scaffold 1 can be independently selected from hydrogen, halogens, hydroxyls, alkoxys, straight aliphatics, branched aliphatics, cyclic aliphatics, heterocyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, sugars, sugar mimics, derivatives thereof, or combinations thereof as well as other well-known chemical substituents. The aliphatic groups can include carbon chains, each independently being about 0-20, about 1-10, or about 1-5 carbons, which carbons may be substituted with hetero atoms O, N, S, P, or the like. The linker can include a straight aliphatic, branched aliphatic, cyclic aliphatic, heterocyclic aliphatic, substituted aliphatic, unsubstituted aliphatic, saturated aliphatic, unsaturated aliphatic, aromatic, polyaromatic, substituted aromatic, hetero-aromatic, amine, primary amine, secondary amine, tertiary amine, aliphatic amine, carbonyl, carboxyl, amide, ester, amino acid, peptide, polypeptide, sugars, sugar mimic, derivatives thereof, or combinations thereof as well as other well-known chemical linkers.

In one embodiment, $R^1$ or $R^2$ of Scaffold 1 can be independently a sugar, sugar mimic, acetyl, N-methyl-4-piperidine and N—N-dimethyl ethyl amine, or 1-methylpiperidine, N,N-dimethylpropan-1-amine. The substituent for $X^1$ or $X^2$ can be independently hydrogen or methoxy. The substituent for $Y^1$ or $Y^2$ can be a methyl or methoxy. The linker can include a saturated or unsaturated aliphatic having $C_3$-$C_{10}$, a 1-1'-biphenyl with a methoxy substituent on each phenyl ring, a 6H-benzo[c]chromene compound, 6,7-dihydrodibenzo[b,d]oxepine, or 7,8-dihydro-6H-dibenzo[b,d]oxocine. For example, the linker can be L1, L2, or L3 as shown, with n for L1 being 0, 1, 2, or 3, and n for L3 being 1, 2, or 3.

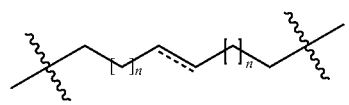
L1

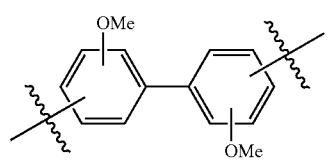
L2

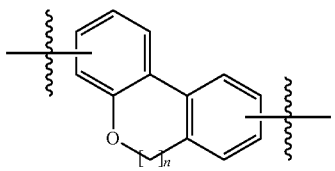
L3

In one embodiment, $R^1$ or $R^2$ for Scaffold 1 can be independently acetyl, noviose sugar (e.g., (3S,4S,5S(-5-methoxy-6,6-dimethyltetrahydro-2H-pyran-3,4-diol, N-methyl-4-piperidine and N—N-dimethyl ethyl amine), or 1-methylpiperidine, N,N-dimethylpropan-1-amine, or derivative thereof. The $R^1$ or $R^2$ can be S1, S2, or S3 or isomers thereof. In one aspect, the noviose sugar or derivative thereof does not include the 3'-substituted noviose sugar of Coumermycin A1.

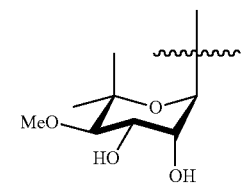
S1

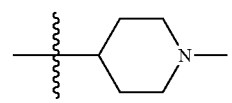
S2

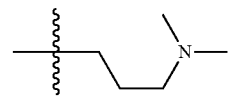
S3

In one embodiment, Scaffold 1 can be devoid of a pyrrole linker or a linker containing an aryl, heteroaryl or olefin. In one aspect, Scaffold 1 can include a pyrrole linker or a linker containing an aryl, heteroaryl or olefin when one or more of $R^1$, $R^2$, $X^1$, $X^2$, $Y^1$, or $Y^2$ is substituted with a substituent described herein, such as a substituent not on coumermycin A1. Examples of suitable substituents can be the specific examples described herein, such as $R^1$ and/or $R^2$ being sugar, sugar mimic, acetyl, N-methyl-4-piperidine and N—N-dimethyl ethyl amine, 1-methylpiperidine, N,N-dimethylpropan-1-amine, or $X^1$ or $X^2$ being independently H or methoxy, or $Y^1$ or $Y^2$ being independently methyl, or methoxy. When $R^1$ or $R^2$ includes a noviose sugar it can be unsubstituted so that it is different from the noviouse sugar on coumermycin A1.

In one embodiment, the coumermycin A1 analog has a structure of Scaffold 2, with: $R^1$ or $R^2$ or $X^1$ or $X^2$ or $Y^1$ or $Y^2$ being the same as described for Scaffold 1, and n and m being independently from, 0-10, 1-4, 1-3, or 1 or 2.

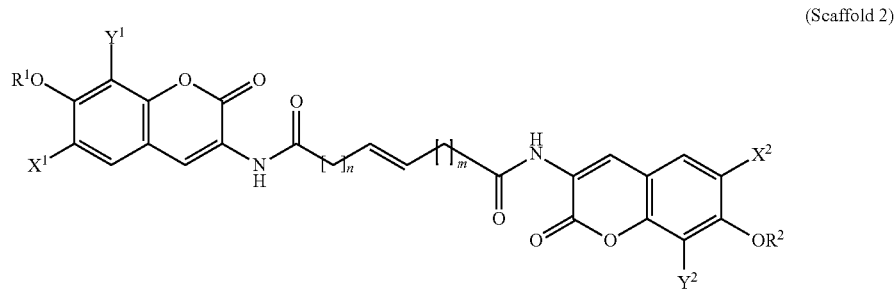

(Scaffold 2)

In one embodiment, wherein the coumermycin A1 analog has a structure of Scaffold 3, with: n being from 0-10, 1-4, 1-3, or 1 or 2.

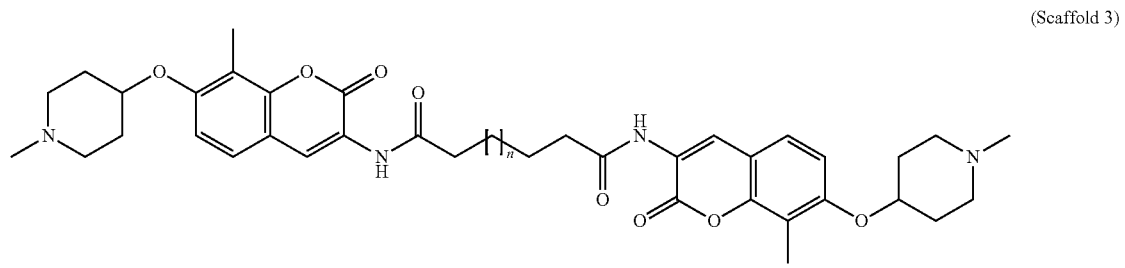

(Scaffold 3)

In one embodiment, the coumermycin A1 analog can have a structure of Scaffold 4, with $R^1$ or $R^2$ being as described for Scaffold 1. Scaffold 4 can be configured with an angle between two coumarin planes with no C—C bond rotation allowed in the linker. As such, the coumermycin A1 analog can be conformationally constrained. Also, Scaffold 3 can be configured with: n=0, 2,6-dicarboxamide, pseudo-trans; n=1, 4,8-dicarboxamide, pseudo-trans; n=1, 3,8-dicarboxamide, trans; n=1, 2,8-dicarboxamide, pseudo-cis; or n=2, 2,6-dicarboxamide, pseudo-trans. The structure of Scaffold 4 is conformationally fixed. The crossed out rotation arrow shows that the linker is fixed and not able to rotate.

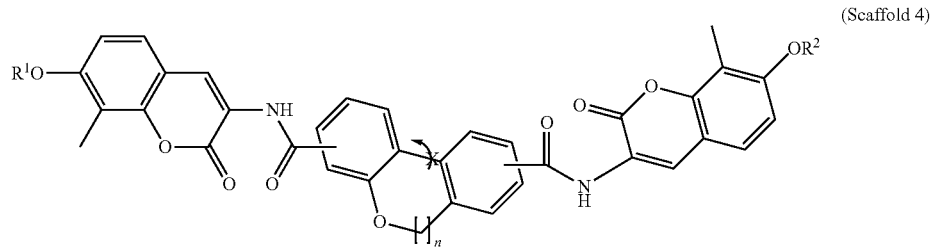

(Scaffold 4)

In one embodiment, the coumermycin A1 analog can have a structure of Scaffold 5, where X can be the same as described for $X^1$ or $X^2$, and Y can be the same as described for $Y^1$ or $Y^2$, and n can be from 0-10, 1-4, 1-3, or 1 or 2.

(Scaffold 5)

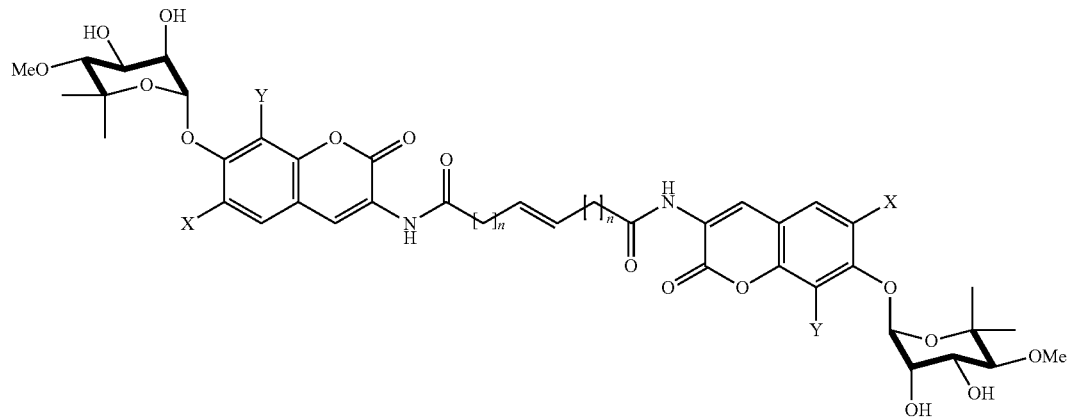

In one embodiment, the coumermycin A1 analog can have a structure of Scaffold 6, where R can be the same as described for $R^1$ or $R^2$, X can be the same as described for $X^1$ or $X^2$, and Y can be the same as described for $Y^1$ or $Y^2$, and n can be from 1-4.

(Scaffold 6)

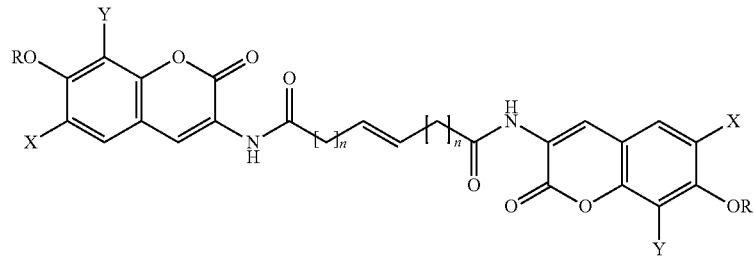

In one embodiment, the coumermycin A1 analog can have a structure of Scaffold 7, where n can be from 0-10, 1-4, 1-3, or 1 or 2.

(Scaffold 7)

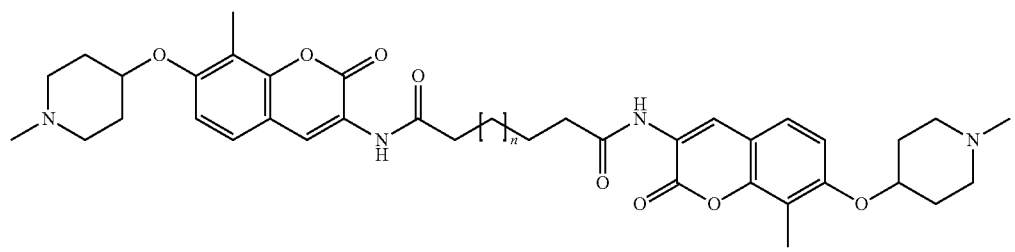

In one embodiment, the coumermycin A1 analog can have a structure of Scaffold 8, where $R^4$ and $R^5$ can be the same as described for $R^1$ or $R^2$ or $X^1$ or $X^2$ or $Y^1$ or $Y^2$, X can be the same as described for $X^1$ or $X^2$, and Y can be the same as described for $Y^1$ or $Y^2$. Specific examples of $R^4$ and $R^5$ include methyl and methoxy.

In one embodiment, substituents $R^1$ or $R^2$ or $X^1$ or $X^2$ or $Y^1$ or $Y^2$ can independently be any aromatic group that is monocyclic or polycyclic, such as benzene groups, toluene groups, ethylbenzene groups, p-xylene groups, m-xylene groups, mesitylene groups, durene groups, 2-phenylhexane groups, (Scaffold 8)

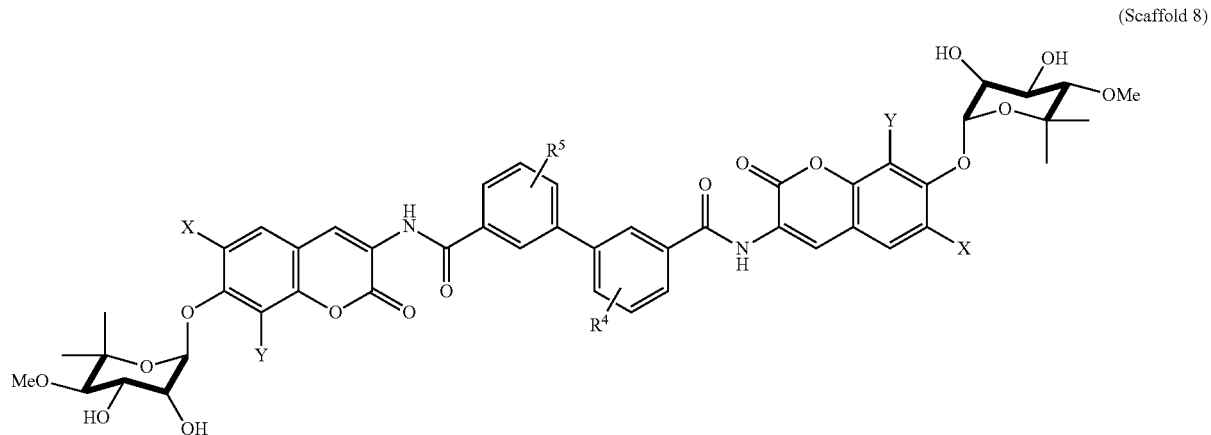

In one embodiment, the coumermycin A1 analog can have a structure of Scaffold 9, where $R^3$ can be the same as described for $R^1$ or $R^2$.

biphenyl groups, phenol groups, aniline groups, nitrobenzene groups, benzoic acid groups, naptholene groups, acenaphthene, acenapthylene, anthracene, chrysene, fluoranthene, (Scaffold 9)

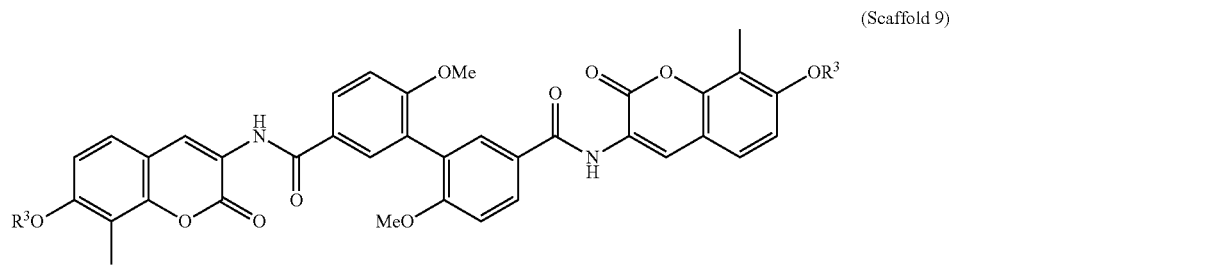

In one embodiment, the coumermycin A1 analog can have a structure of Scaffold 10, where n can be from 0-4, or from 1-3, or 1 or 2.

phenathrene, pyrene, coronene, corannulene, tetracene, pentacene, triphenelene, ovalene, or combinations thereof or derivatives thereof, whether substituted or unsubstituted.

(Scaffold 10)

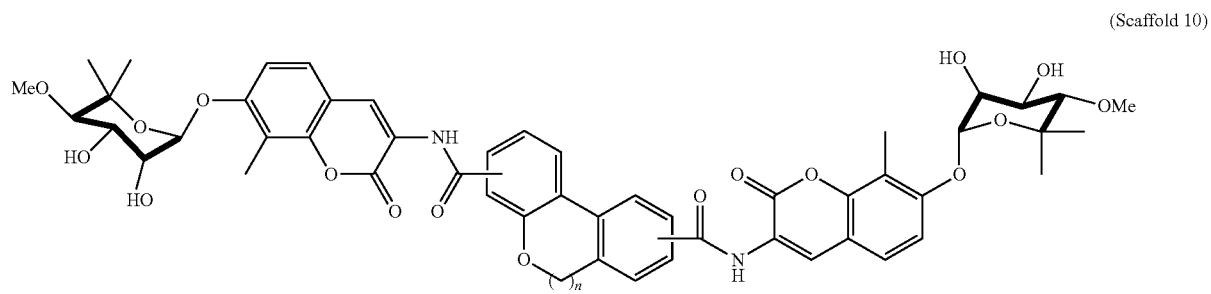

In one embodiment, the coumermycin A1 analog can have substituents in accordance with one of the Tables 1-6 provided below.

In one embodiment, the coumermycin A1 analog can have one or more 7 membered rings in the linker between the coumarin residues.

When substituted, the substituents can be as described herein. The substituents can also include hetero atoms.

In one embodiment, substituents $R^1$ or $R^2$ or $X^1$ or $X^2$ or $Y^1$ or $Y^2$ can independently be selected from any amino acid side group so that the amino acid is selected from positively charged amino acids, arginine, histidine, lysine, negatively charged amino acids, aspartic acid, glutamic acid, polar uncharged amino acids, serine, threonine, asparagine, glutamine, cysteine, selenosystein, glycine, proline, hydrophobic amino acids, alanine, valine, isoleucine, methionine, phenylalanine, tyrosine, tryptophan, other amino acids, non-standard amino acids, carnitine, hydroxyproline, selenomethionine, lanthionine, 2-aminoisobutyric acid, dehydroalanine, gamma-aminobutyric acid, ornithine, citrulline, beta alanine, pantothenic acid, or derivatives thereof.

The structure of the coumermycin A1 can be modified and different from coumermycin A1. In one aspect, the coumermycin A1 analog can have a piperidine ring in place of the substituted noviose sugar. In one aspect, the coumermycin A1 analog can be devoid of a noviosyl group. In one aspect, the coumermycin A1 analog can have a heterocycle. In one aspect, the coumermycin A1 analog can have an 8-methyl group of coumermycin A1 being replaced with an 8-methoxy group. That is, the 8-methyl group can be replaced with a 8-methoxy group. In one aspect, the coumermycin A1 analog can have a N-methyl-4-piperidine or N,N-dimethyl ethyl amine. In one aspect, the coumermycin A1 analog can have a 5-methylpyrrole linker of coumermycin A1 being replaced with a bicyclic, tricyclic, or other flexible tether. That is, the coumermycin A1 analog can include a bicyclic, tricyclic, or other flexible tether and be devoid of a 5-methylpyrrole linker. In one aspect, the coumermycin A1 analog can have a 6- and/or 8-methoxy group.

In one embodiment, the coumermycin A1 analog can have an alkyl group in place of a methyl group on coumermycin A1. In one aspect, the coumermycin A1 analog can have a 6-alkoxy and/or 8-alkoxy group. In one aspect, the coumermycin A1 analog be described as being a 6,8-disubstituted coumarin A1 analog. In one aspect, the coumermycin A1 analog can include a biaryl or tricycle containing linker between the coumarin residues.

In one aspect, the coumermycin A1 analog can have a structure of one of Compounds 16-19, 26-36, 38, 42-44, 65-73, or 101-105 as recited herein, more particularly, Compounds 26-36, 38, 42-44, 65-73, or 101-105, and even more particularly Compounds 26-36. In one aspect, the coumermycin A1 analog can have a structure of Compound 38. In one aspect, the coumermycin A1 analog can have a structure of one of Compounds 42-44. In one aspect, the coumermycin A1 analog can have a structure of one of Compounds 65-73. In one aspect, the coumermycin A1 analog can have a structure of one of Compounds 101-105. The structures of these compounds are described in the tables below.

Any of the chemical terms described herein are defined by their standard chemical definitions.

EXPERIMENTAL

The retrosynthesis of coumermycin A1 analogs is depicted in Scheme 1. The sugar-substituted coumarins were prepared as previously described. See: Donnelly, A.; Mays, J. R.; Burlison, J. A.; Nelson, J. T.; Vielhauer, G.; Holzbeierlein, J.; Blagg, B. S. J. *J. Org. Chem.* 2008, 73, 8901; Donnelly, A. C.; Zhao, H.; B., R. K.; Blagg, B. S. J. *Med. Chem. Comm.* 2010, 1, 165; Zhao, H.; B., R. K.; Blagg, B. S. J. *ACS Med. Chem. Lett* 2010, 1, 311; Burlison, J. A.; Avila, C.; Vielhauer, G.; Lubbers, D. J.; Holzbeierlein, J.; Blagg, B. S. *J. Org. Chem.* 2008, 73, 2130; and Burlison, J. A.; Blagg, B. S. *Org. Lett.* 2006, 8, 4855. Coupling of the sugar-substituted amino-coumarins with either the diacid or diacid chloride linker could then be achieved upon exposure to standard amide forming conditions. FIG. 1 shows Scheme 1, which can be described as a retrosynthesis of coumermycin A1 analogs.

Figure 2:
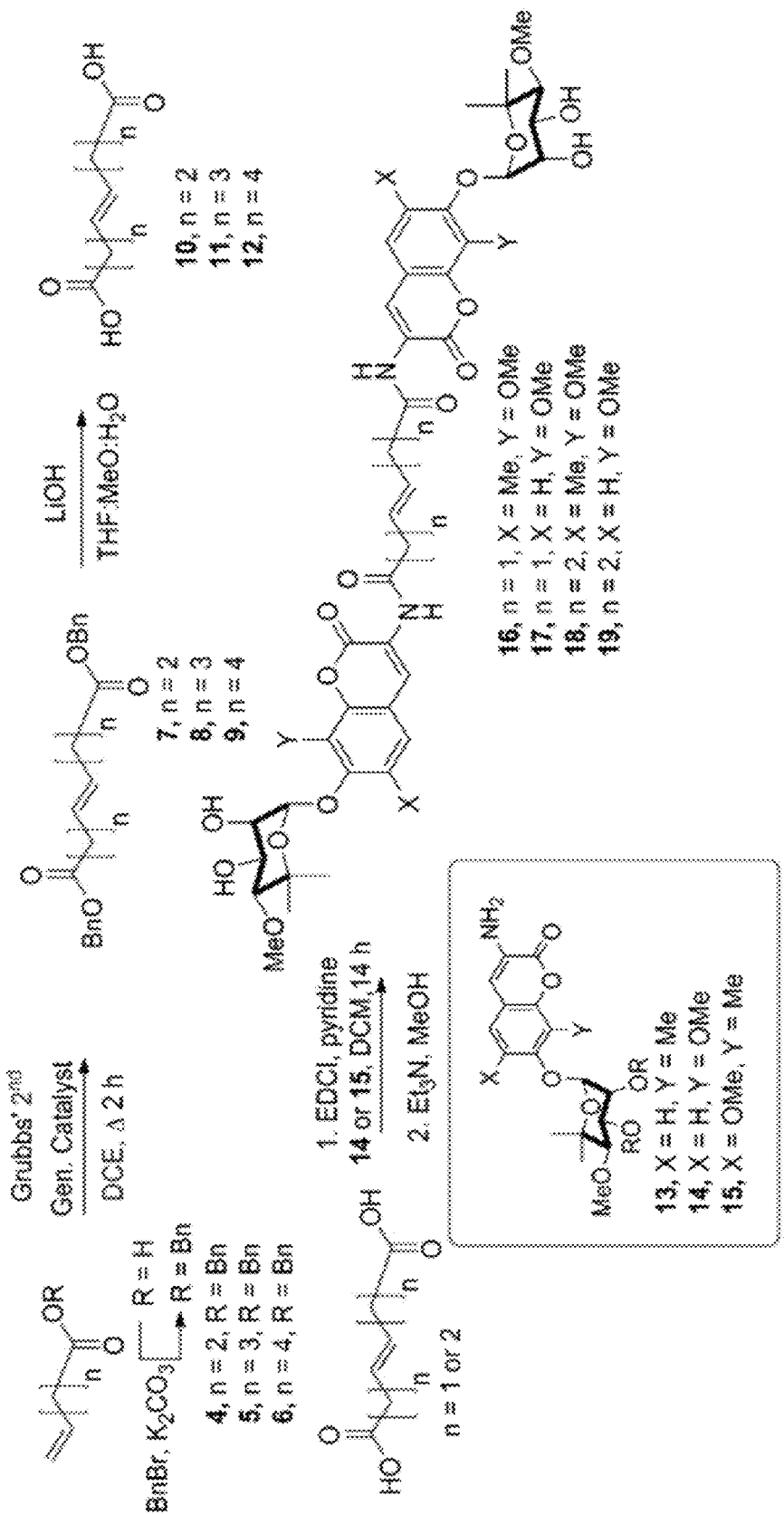
FIG. 2 shows Scheme 2, which can be described as synthesis of noviosylated olefin dimers.

Synthesis and evaluation of olefin and saturated-linkers for coumermycin A1 analogs were conducted. The olefinic tethers were chosen based upon previously reported coumermycin A1 analogs (Burlison, J. A.; Blagg, B. S. *Org. Lett.* 2006, 8, 4855). These linkers varied in length and geometry to identify the optimal distance between the two C-terminal binding sites in the C-2 symmetric, HSP90 homodimer. Previous synthesis of coumermycin A1 analogs resulted in low yields from the cross-metathesis reaction (9-51%) (Burlison, J. A.; Blagg, B. S. *Org. Lett.* 2006, 8, 4855). Therefore, linkers 10-12 (Compounds 10-12) were prepared first and subsequently coupled with amino-coumarins 13-14 (Compounds 13-14), using peptide coupling conditions (Scheme 2). The diacid olefin linkers (Compounds 10-12) were prepared via cross-metathesis of the olefin containing benzyl esters (Compounds 4-6) followed by hydrolysis. Amino-coumarins (Compounds 14 or 15) were coupled with the diacid linkers (Compounds 10-12) using EDCI in a mixture of pyridine and methylene chloride, which after solvolysis of the cyclic carbonate, provided coumermycin analogs (Compounds 16-19) in good yield. FIG. 2 shows Scheme 2, which can be described as synthesis of noviosylated olefin dimers.

Figure 3:
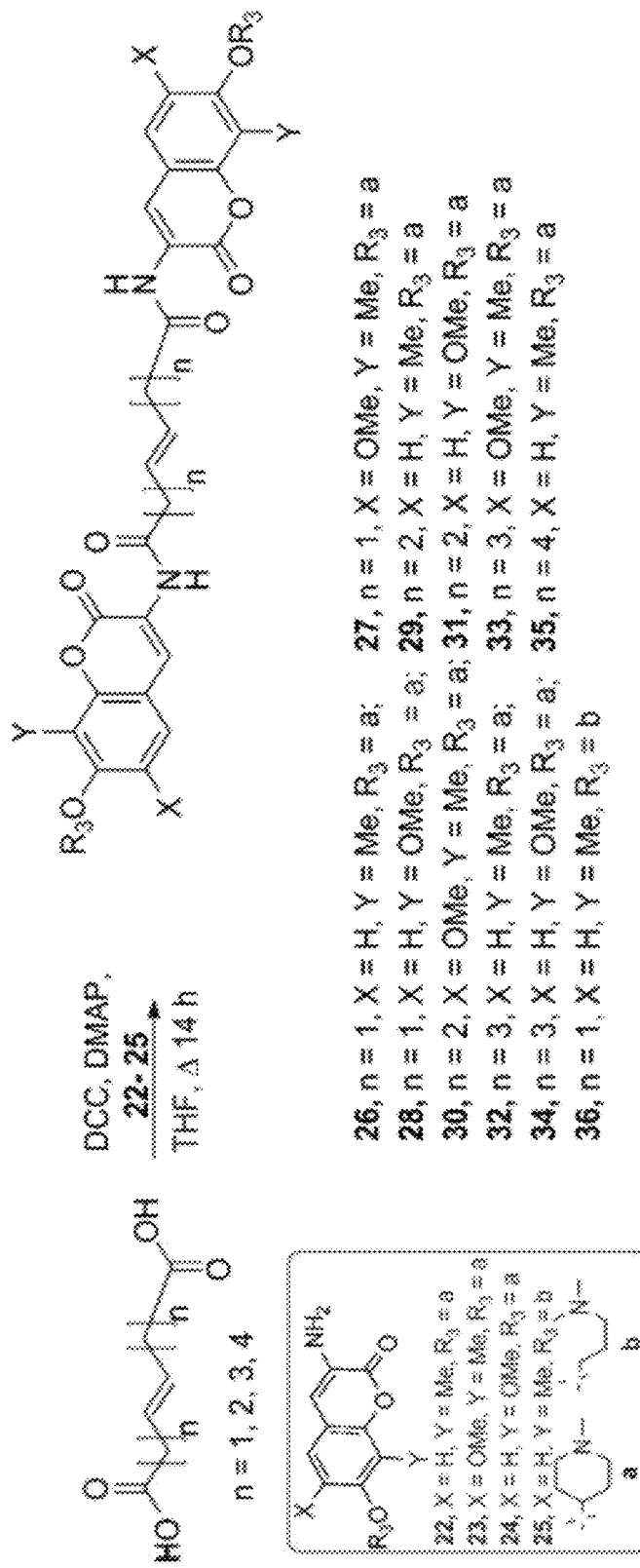
FIG. 3 shows Scheme 3, which can be described as synthesis of olefinic dimers.

Replacement of the stereochemically complex noviose sugar with simple, commercially available amines were sought as outlined in Scheme 2. Dimers of (Compounds 26-36) were prepared utilizing a combination of DCC and DMAP, which produced amines (Compounds 22-25) and olefinic linkers (Compounds 10-12) in good to moderate yields (Scheme 3). FIG. 3 shows Scheme 3, which can be described as synthesis of olefinic dimers.

Once synthesized, the library of coumermycin A1 analogs containing the olefinic and saturated linkers, were evaluated for anti-proliferative activity against SKBr3 (estrogen receptor negative, Her2 over-expressing breast cancer cells), MCF-7 (estrogen receptor positive breast cancer cells), A549 (human lung adenocarcinoma epithelial), HT29 (Human colon adenocarcinoma grade II), and PC3mm2 (androgen receptor insensitive prostate cancer) cell lines. The activities produced provide insight into the optimal distance between binding sites and provide rationale for subsequent analog design. As shown in Table 1, the eight-carbon olefin linker dimers (Compounds 18 and 19) were more efficacious than the analogous six-carbon linkers, Compound 16 and Compound 17, while substitution at the 6-position of the coumarin ring exhibited minimal effect on inhibitory activity. This result was surprising, because for the monomeric inhibitors, the 6-OMe-8-Me (Compound 16 and Compound 18) and 8-OMe coumarins (Compounds 17 and 19) produced compounds with enhanced activity as compared to the 8-Me derivative. This suggests the dimers may bind in an altered orientation as compared to the monomeric novobiocin analogs, or at a different point in the chaperone cycle. As shown, X is at the 6 position and Y is at the 8 position.

TABLE 1

Anti-Proliferation Activities of Noviosylated Olefin Dimers in μM.

| Entry | n | X | Y | SKBr3 | MCF-7 |
|---|---|---|---|---|---|
| 16 | 1 | OMe | Me | >100[a] | >100 |
| 17 | 1 | H | OMe | 52.0 ± 7.8 | >100 |
| 18 | 2 | OMe | Me | 105.7 ± 13.2 | 168.0 ± 9.7 |
| 19 | 2 | H | Me | 4.1 ± 0.5 | 2.61 ± 0.8 |
| 20 | 1 | H | Me | >100 | 53.1 ± 7.1 |
| 21 | 2 | H | Me | 1.5 ± 0.1 | 3.9 ± 0.7 |

[a]Values represent mean ± standard deviation for at least two separate experiments performed in triplicate, all values presented in μM To determine the optimal distance between the coumarin moieties in non-noviosylated coumermycin A1 dimers (Compounds 26-36), a series of compounds were prepared that contain an increasing number (6, 8, 10 and 12) of methylene units in the linker. Compounds 26-36 were found to be 10-100 fold more potent than the corresponding noviosylated coumermycin A1 analogs, Compounds 16-19. In the case of 8-methyl coumarin, the 8-carbon linker dimer present in Compound 29 is slightly more active than the 6-carbon linker, Compound 26, and 2-3 fold more active than the 10-carbon linker (Compound 32). Interestingly the 10-carbon dimer, Compound 32, was 10-20 fold more active than any other dimer against prostate cancers, manifesting low nanomolar anti-proliferative activities (~200-400 nM). In general, compounds containing either the 8-OMe/6-OMe or 8-OMe coumarin substitution were found to be more efficacious against prostate cancer cell lines than their 8-Me counterparts.

TABLE 2

Anti-Proliferation Activities of non-Noviosylated Olefin Dimers.

| # | R | n | X | Y | SKBr3 | MCF7 | PC3mm2 | A549 | HT29 |
|---|---|---|---|---|---|---|---|---|---|
| 26 | 4-piperidinyl | 1 | H | Me | 0.18 ± 0.03[a] | 0.29 ± 0.01 | 7.51 | 8.84 | 7.1 |
| 29 | 4-piperidinyl | 2 | H | Me | 0.15 ± 0.01 | 0.27 ± 0.02 | 4.19 | 5.54 | 0.05 |
| 32 | 4-piperidinyl | 3 | H | Me | 0.89 ± 0.01 | 0.63 ± 0.03 | 0.44 | 0.22 | 0.24 |

TABLE 2-continued

Anti-Proliferation Activities of non-Noviosylated Olefin Dimers.

[Structure: dimeric coumarin with RO, X, Y substituents connected by olefin linker with (CH2)n groups]

| # | R | n | X | Y | SKBr3 | MCF7 | PC3mm2 | A549 | HT29 |
|---|---|---|---|---|-------|------|--------|------|------|
| 35 | piperidinyl-methyl | 4 | H | Me | 0.51 ± 0.06 | 0.73 ± 0.10 | NT | NT | NT |
| 27 | piperidinyl-methyl | 1 | OMe | Me | 0.27 ± 0.01 | 0.56 ± 0.05 | 0.17 | 0.55 | NT |
| 30 | piperidinyl-methyl | 2 | OMe | Me | 1.10 ± 0.13 | 1.31 ± 0.1 | 4.86 | 13.4 | NT |
| 33 | piperidinyl-methyl | 3 | OMe | Me | 0.22 ± 0.05 | 0.31 ± 0.05 | 0.38 | 37.7 | NT |
| 28 | piperidinyl-methyl | 1 | H | OMe | 0.71 ± 0.04 | 1.46 ± 0.2 | 8.63 | NT | NT |
| 31 | piperidinyl-methyl | 2 | H | OMe | 2.22 ± 0.5 | 1.12 ± 0.03 | 0.06 | 1.22 | NT |
| 34 | piperidinyl-methyl | 3 | H | OMe | 0.37 ± 0.05 | 0.88 ± 0.11 | 0.05 | 1.21 | NT |
| 36 | N-methyl-aminoethyl | 1 | H | Me | 0.46 ± 0.02 | 0.84 ± 12 | 15.2 | 19.4 | 12.2 |
| 38 | piperidinyl-methyl (cis-isomer) | 2 | H | Me | >100 | 49.9 ± 2.6 | 32.9 | 77.6 | NT |

$^a$Values represent mean ± standard deviation for at least two separate experiments performed in triplicate, all values presented in μM For comparison, saturated dimers (Compounds 42-44) were prepared by coupling the commercially available diacid chlorides (Compounds 39-41) with amino-coumarin (Compound 22) excellent yield (see Scheme 4). The 8-carbon, cis-olefin containing linker 38 was also prepared for direct comparison to the trans-isomer (Compound 29). FIG. 4 shows Scheme 4, which can be described as synthesis of saturated- and cis-dimers.

The effect of saturation and conformational flexibility was evaluated by measurement of their antiproliferative activity against cancer cells. In general, saturated analogs (Compounds 42-44) were less active than the corresponding trans-olefin containing dimers, which were more active than cis-isomer, (Compound 38). It appears as though the trans-olefin can orient the coumarin rings into a more favorable conformation, while the cis-olefin appears to disrupt the orientation of the coumarin rings. Since the saturated linker is flexible, it allows the coumarin rings to achieve a favorable conformation, but elicits an entropic penalty, manifesting activity that is between the cis- and trans-isomers.

TABLE 3

Anti-Proliferation Activities of Saturated Linker Dimers.

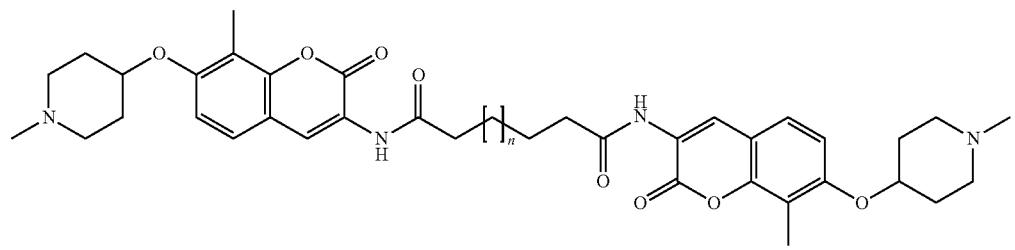

| Entry | n | SKBr3 | MCF-7 | PC3mm2 | A549 | HT29 |
|---|---|---|---|---|---|---|
| 42 | 1 | 1.26 ± 0.2[a] | 2.46 ± 0.4 | NT | NT | NT |
| 43 | 3 | 1.19 ± 0.3 | 2.82 ± 0.3 | 13.8 | 30.4 | 26.3 |
| 44 | 5 | 2.84 ± 0.1 | 3.68 ± 0.4 | 10.2 | 13.2 | 3.9 |

Figure 5A:
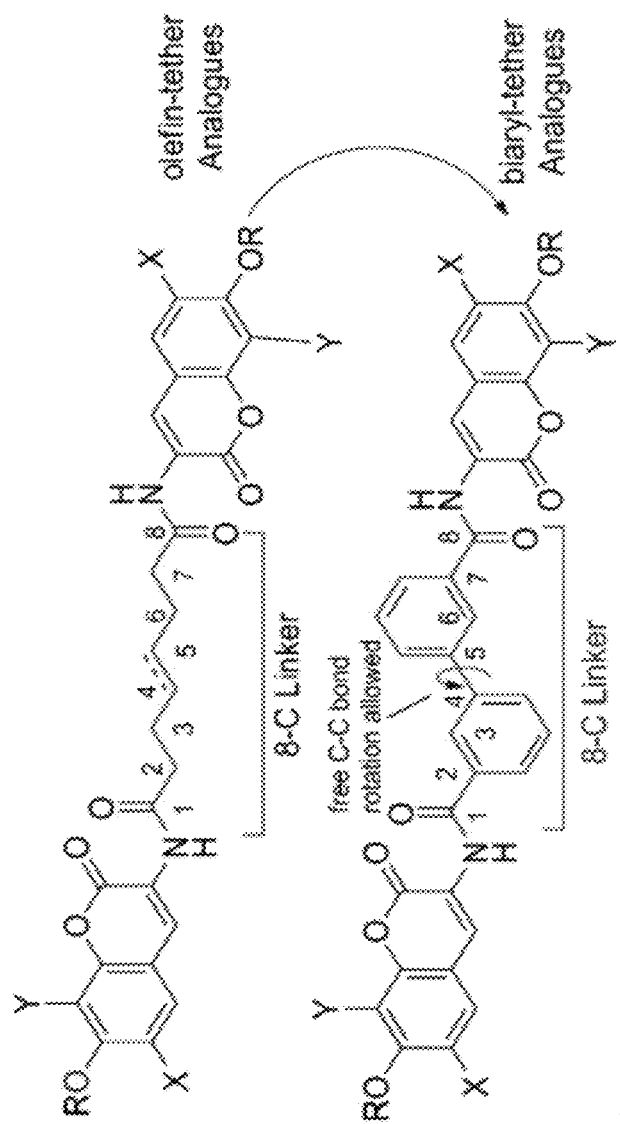
FIG. 5A shows the rational for biaryl-tether analogs.
Figure 5B:
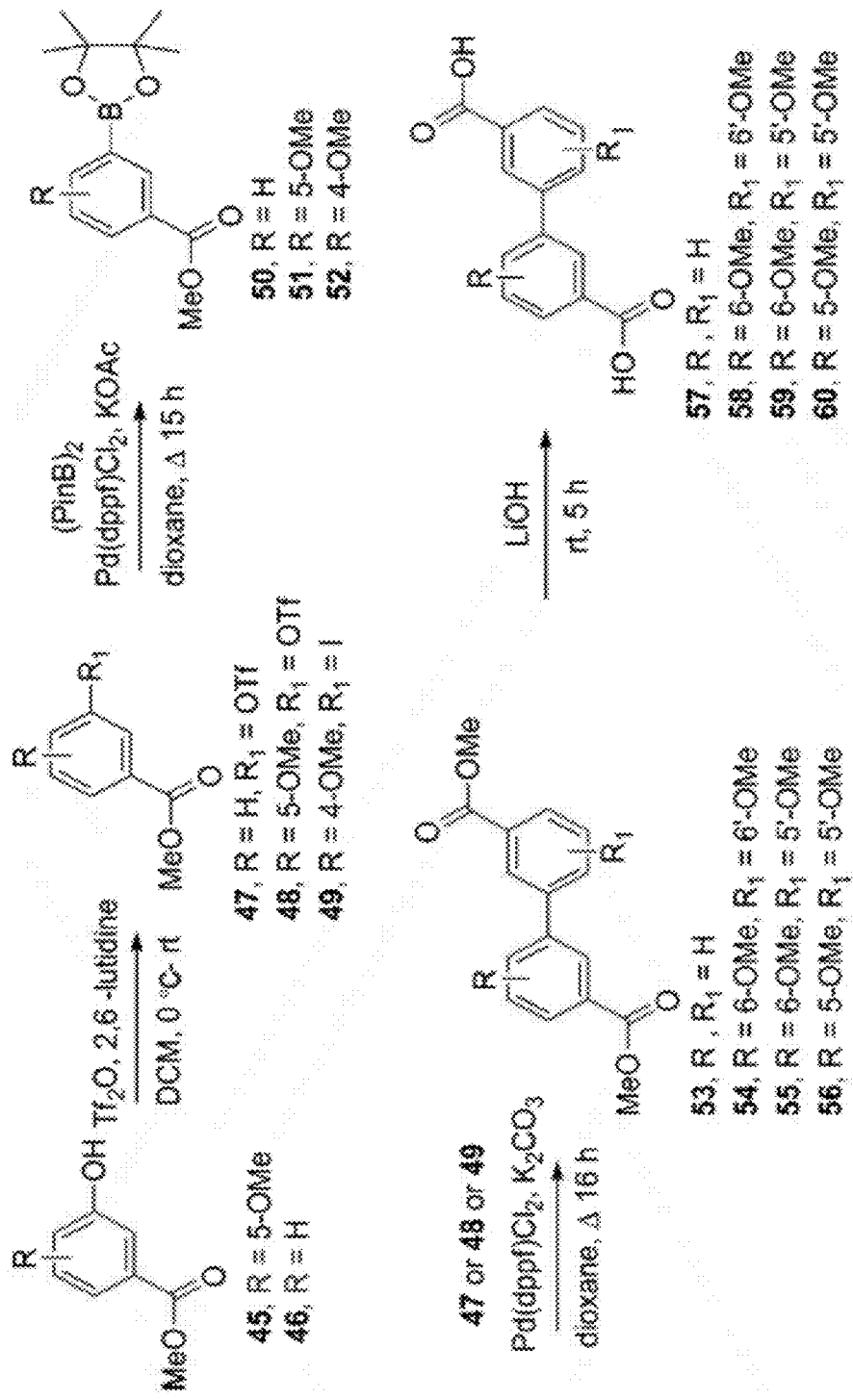
FIG. 5B shows Scheme 5, which can be described as synthesis of conformationally flexible biaryl linkers.

[a]Values represent mean ± standard deviation for at least two separate experiments performed in triplicate, all values presented in μM Synthesis of biaryl-tether coumermycin A1 analogs was conducted. After preparation of the olefin-containing linkers, conformationally constrained analogs were prepared to include a tether that represents the optimal length, and also includes the biaryl ring system present in the monomeric inhibitors. The biaryl system was chosen because it allows rotation between the biaryl rings, resulting in multiple conformations and mimicking the trans double bond found in (Compound 29). Additionally, as shown in FIG. 5A, which shows the rational for biaryl-tether analogs, inclusion of the biaryl side chain places the two coumarin rings at a distance that corresponds to the length observed for 8 carbons. Although slight conformational flexibility is produced by this motif, π-stacking attributes may also be manifested by these molecules, which is believed to be responsible for the increased inhibitory activities manifested by monomeric species that contain this ring system. To validate this hypothesis, biaryl linkers (Compounds 57-60) containing various patterns of substitution that mimic potential orientations of the methoxy groups were prepared. Synthesis of the biaryl linkers commenced with phenols (Compounds 45 and 46). Conversion of Compound 45 or Compound 46 to the triflate Compound 47 or Compound 48 or Compound 49, followed by conversion to the boronic ester, allowed subsequent Suzuki coupling with iodo- or -triflate containing compounds (Compound 47, 48 or 49), to afford biaryl diesters (Compounds 53-56) in good yield. FIG. 5B shows Scheme 5, which can be described as synthesis of conformationally flexible biaryl linkers.

Diesters (Compounds 53-56) were then hydrolyzed to the corresponding diacids, (Compounds 57-60), and subsequently converted to diacid chlorides before coupling with amino-coumarins (Compounds 13-15) to produce the biaryl-linked noviose-containing dimers (Compounds 65-70) upon hydrolysis of the cyclic carbonate. Diacid chloride (Compound 62) was also coupled with amino-coumarins (Compounds 22 and 25), to give biaryl dimers with modified sugars (Compounds 71-73) in excellent yields. FIG. 6 shows Scheme 6, which can be described as a synthesis of biaryl noviosylated dimers.

Synthesis of tricyclic-tether coumermycin A1 analogs was conducted. To further assess conformational flexibility and optimal coumarin ring geometry, conformationally constrained biaryl analogs were synthesized. The tricyclic linkers containing varying bridges of 5, 6 or 7 atoms would yield dimers that exhibit decreasing flexibility in their prescribed conformations. The 5-6- and 7-membered tricyclic tethered linkers (Compounds 91, 92, and 95) were designed alongside the pseudo cis and trans 6-membered tethered tricycles in an effort to elucidate the orientation by which these molecules bind HSP90 (Scheme 3). Scheme 3 provides rationale for tricyclic-tether coumermycin A1 analogs.

Retrosynthetic analysis of the tricyclic-containing coumermycin A1 analogs is depicted in Scheme 7, in which two molecules containing sugar substituted amino-coumarins (Compound 13) can be coupled with the tricyclic diacid chloride. Tricyclic tethers (Compounds 76 and 81-83) were envisioned to be prepared via nucleophilic displacement of methyl 4-(bromomethyl)-3-iodobenzoate or methyl 3-bromo-4-fluorobenzoate with methyl salicylate, followed by an intermolecular Heck-cyclization. FIG. 7 shows Scheme 7, which can be described as retrosynthesis of 5- and 6-membered tricyclic-tether analogs.

Figure 8:
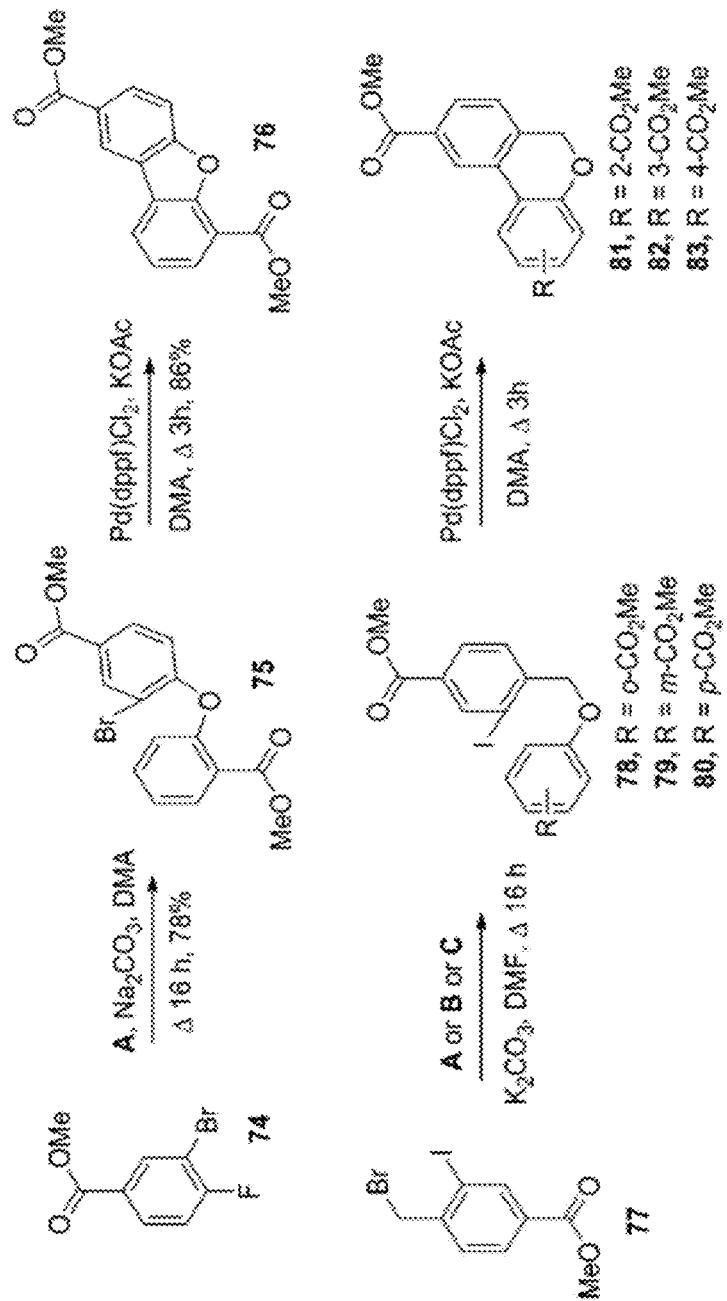
FIG. 8 shows Scheme 8, which can be described as synthesis of 5- and 6-membered tricyclic tether.

Preparation of the five-membered tricyclic tether commenced by coupling methyl 3-bromo-4-fluorobenzoate (Compound 74) with methyl salicylate enlisting sodium carbonate in N—N-dimethylacetamide to provide biaryl ether (Compound 75) in moderate yield. Intra-molecular Heck-cyclization of biaryl ether (Compound 75) afforded the 5-membered tricyclic tether, Compound 76, in good yield. FIG. 8 shows Scheme 8, which can be described as synthesis of 5- and 6-membered tricyclic tether.

Figure 9:
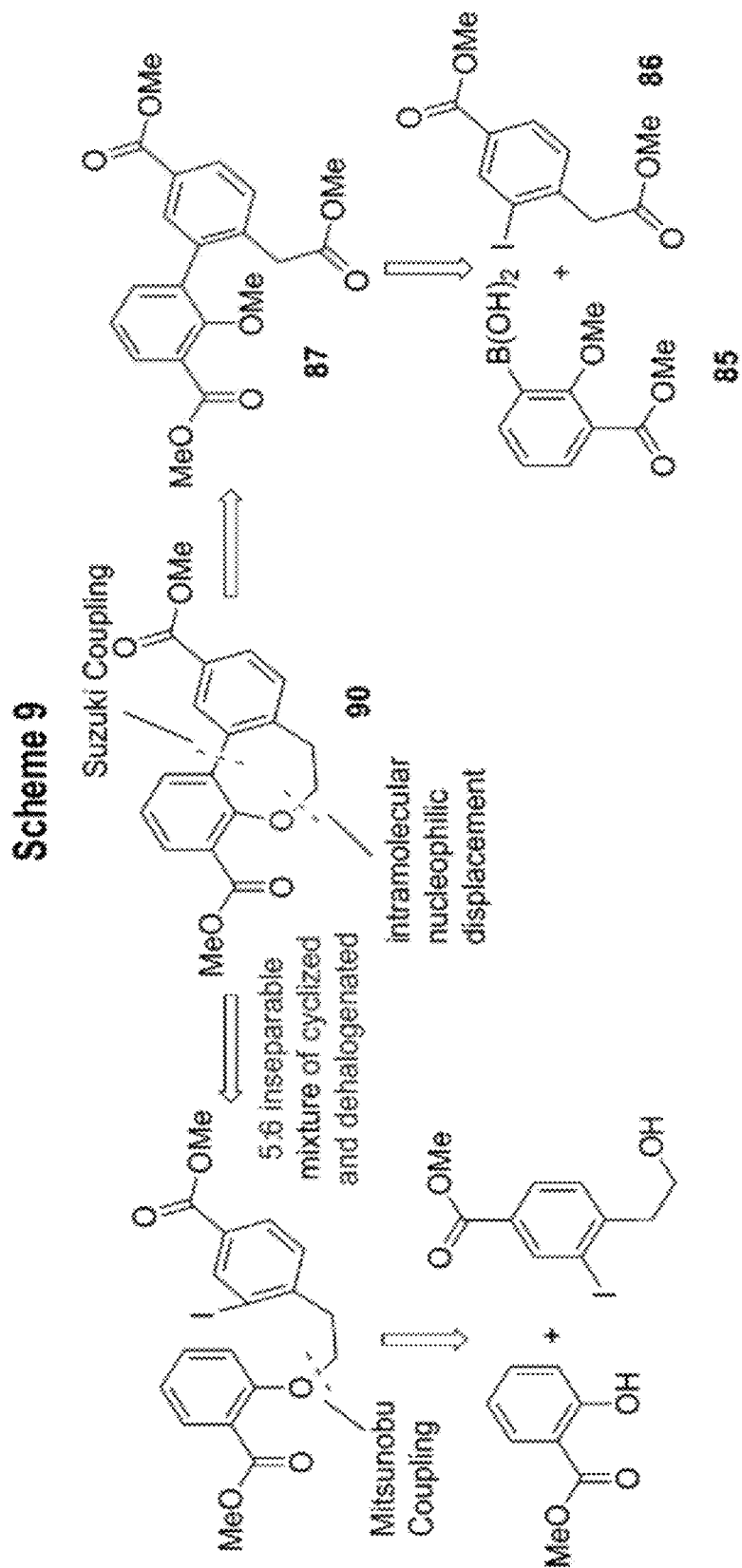
FIG. 9 shows Scheme 9, which can be described as retrosynthetic analysis of 7-membered tricyclic-tether.

Six-membered tethers (Compounds 81-83) were prepared by coupling o-, m- or p-methyl salicylate with methyl 4-(bromomethyl)-3-iodobenzoate (Compound 77) to obtain iodo benzyl ethers (Compounds 78-80), which were subjected to an intra-molecular Heck-cyclization to give the 6-membered products, (Compounds 81-83), in excellent yields. Initially, preparation of the seven-membered tether (Compound 90) was approached similarly, but the Heck-cyclization produced an inseparable (5:6) mixture of cyclized and de-halogenated compounds (Scheme 9). Consequently, the biaryl bond was constructed first, followed by cyclization to afford the seven-membered tether, Compound 90. FIG. 9 shows Scheme 9, which can be described as retrosynthetic analysis of 7-membered tricyclic-tether.

Figure 10:
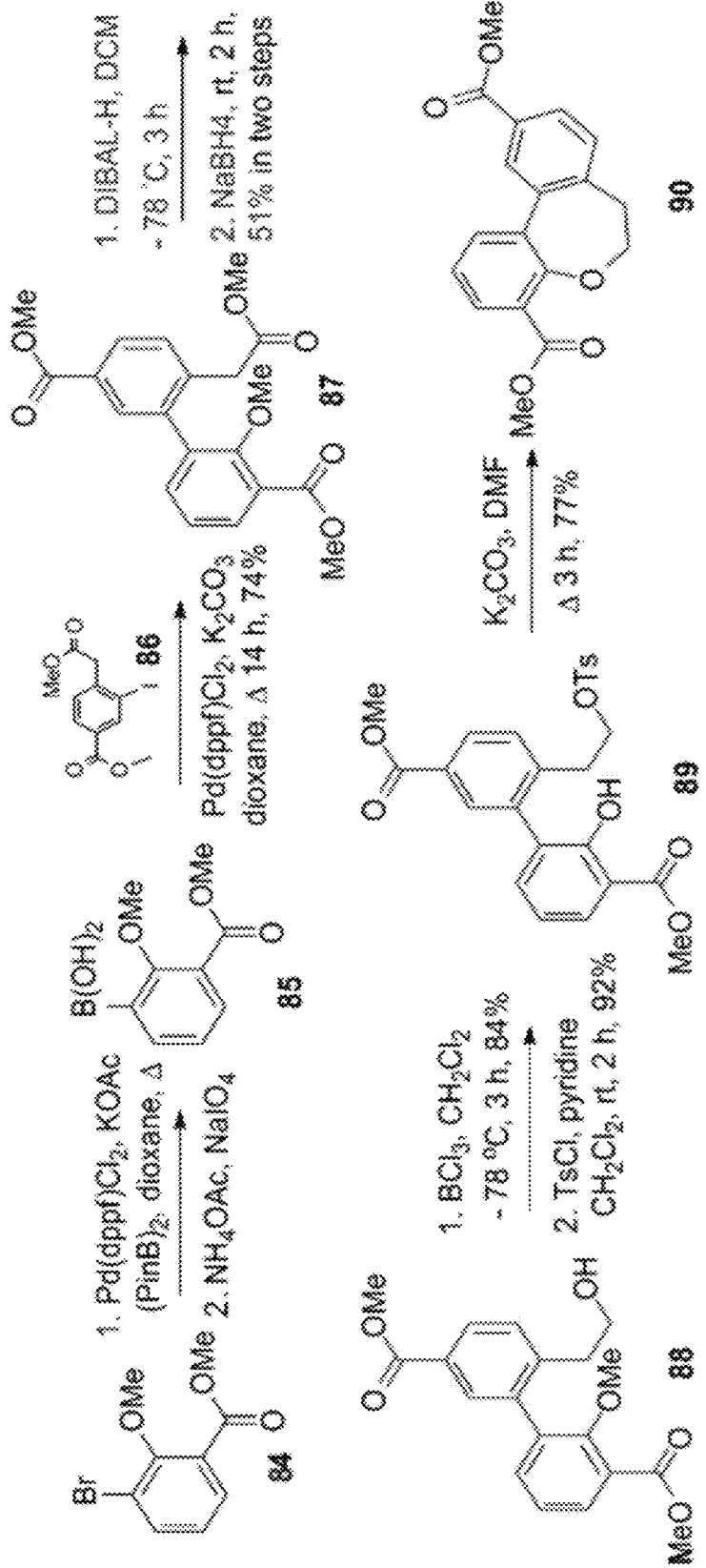
FIG. 10 shows Scheme 10, which can be described as synthesis of 7-membered tether.

Synthesis of Compound 90 commenced with methyl 3-bromo-2-methoxybenzoate (Compound 84), which was converted to boronic acid (Compound 85) in two steps. The boronic acid was coupled with methyl 3-iodo-4-(2-methoxy-2-oxoethyl)benzoate (Compound 86) under standard Suzuki coupling conditions to yield triester (Compound 87). After which, the ester was selectively reduced to alcohol (Compound 88), followed by cleavage of the methyl ether to give the free phenol. The aliphatic alcohol was converted to the tosylate (Compound 89) and subjected to intramolecular cyclization in the presence potassium carbonate to give the seven-membered product, (Compound 90) in good yield, and with only trace amounts of product resulting from elimination that gave the corresponding styrene. FIG. 10 shows Scheme 10, which can be described as synthesis of 7-membered tether.

Figure 11:
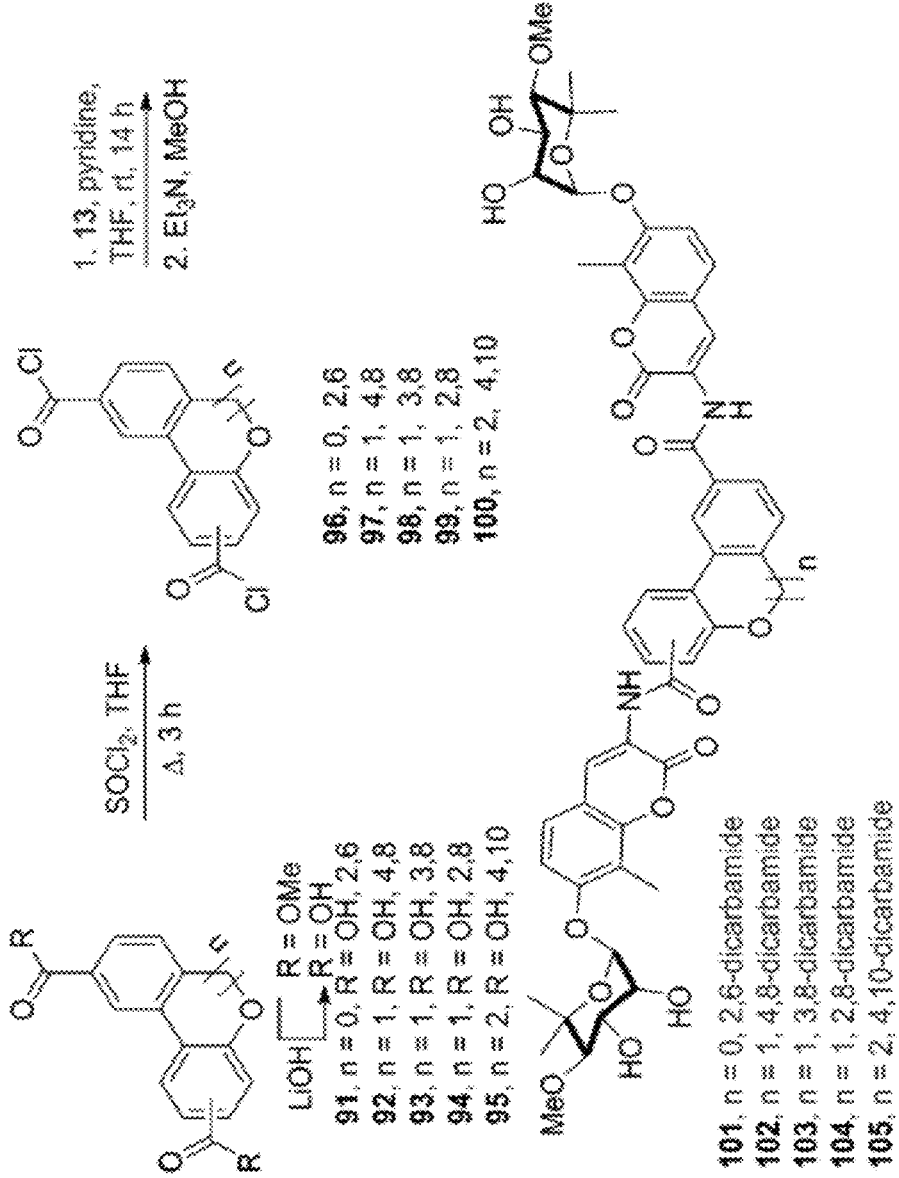
FIG. 11 shows Scheme 11, which can be described as synthesis of tricyclic tether noviosylated dimers.

Upon preparation, the 5, 6, and 7-membered tricyclic esters were hydrolyzed, converted to the corresponding diacid chlorides, Compounds 96-100, and coupled with amino-coumarin (Compound 10) to provide the requisite dimers (Compounds 101-105) following hydrolysis (Scheme 11). FIG. 11 shows Scheme 11, which can be described as synthesis of tricyclic tether noviosylated dimers.

Biological evaluation of biaryl and tricycle coumermycin A1 analogs was conducted. After construction of the olefin and alkane linked dimers, analogs containing biaryl linkers with varying methoxy substitution (Compounds 65-70) and coumarin scaffolds were prepared and subsequently evaluated for anti-proliferative activity (Table 4). To evaluate the effect of the methoxy group, four biaryl linkers (Compounds 65-70) were synthesized. Among these, the symmetrical (Compounds 66 and 68) biaryl dimers were more active than the non-symmetrical analog (Compound 67). Compound 66 (6-OMe, 6'-OMe) was 2-fold more active than Compound 68 (5-OMe, 5'-OMe) against breast cancer cell lines and these compounds were less active against prostate cancer cell lines. Interestingly, the dimer with 8-OMe substitution of the coumarin scaffold (Compound 70) was of equal potency against the breast cancer cell lines as the corresponding 8-Me analog of Compound 66, but was 100-150 fold more active against prostate cancer cell lines. Compound 69 (8-Me and 6-OMe coumarin) was 7-8 fold more active on SkBr3 cell lines and slightly more potent on McF-7 cell lines than its corresponding 8-Me and 8-OMe coumarin analogs (Compounds 66 and 68).

TABLE 4

Anti-Proliferation Activities of Biaryl Dimers.

| Entry | X | Y | R | R[1] | SKBr3 | MCF-7 | PC3mm2 | A549 | HT29 |
|---|---|---|---|---|---|---|---|---|---|
| 65 | H | Me | H | H | 0.86 ± 0.14[a] | 1.26 ± 0.17 | NT | NT | NT |
| 66 | H | Me | 6-OMe | 6'-OMe | 1.16 ± 0.21 | 0.76 ± 0.14 | 36.68 | 36.78 | 36.54 |
| 67 | H | Me | 6-OMe | 5'-OMe | 28.50 ± 4.4 | 38.0 ± 1.5 | NT | NT | NT |
| 68 | H | Me | 5-OMe | 5'-OMe | 1.95 ± 0.4 | 1.85 ± 0.52 | 12.53 | 28.90 | 11.72 |
| 69 | OMe | Me | 6-OMe | 6'-OMe | 0.11 ± 0.05 | 0.72 ± 0.21 | NT | NT | NT |
| 70 | H | OMe | 6-OMe | 6'-OMe | 0.91 ± 0.12 | 0.88 ± 0.2 | 0.27 | 0.21 | 0.27 |

[a]Values represent mean ± standard deviation for at least two separate experiments performed in triplicate, all values presented in μM Analogous dimers to the previously described novobiocin monomer analogs with secondary amine-containing sugar replacements (Compounds 72 and 73) were also evaluated, interestingly these compounds are ~10-fold less active than the corresponding noviosylated coumarin-containing (Compounds 65-70) analogs (Table 5). This trend is opposite to that of the novobiocin series of compounds. Another disadvantage exhibited by Compounds 71 and 72 were their inherent insolubility in DMSO, which may contribute to their modest biological activity.

TABLE 5

Anti-Proliferation Activities Non-Noviosylated Biaryl Dimers.

| Entry | R³ | SKBr3 | MCF-7 | PC3mm2 | A549 | HT29 |
|---|---|---|---|---|---|---|
| 71 | 4-N-methylpiperidinyl | 4.98 ± 0.7 | 14.23 ± 2.3 | NT | NT | NT |
| 72 | dimethylaminoethyl | 9.50 ± 1.2 | 11.66 ± 1.6 | 52.27 | 93.45 | 62.7 |
| 73 | OAc | 11.84 ± 0.8[a] | >100 | NT | NT | NT |

[a]Values represent mean ± standard deviation for at least two separate experiments performed in triplicate, all values presented in μM As mentioned above, we sought to optimize the linker geometry by synthesizing conformationally constrained tricyclic analogs, with ring sizes of 5, 6 and 7 atoms (Compounds 101-105). These tri-cyclic systems allowed the dimers to exhibit geometries that were dependent on ring size and attachment to the coumarin ring. After synthesis of the tricyclic tether analogs (Compounds 101-105) they were evaluated for anti-proliferative activity. Among these analogs, the 6- and 7-membered tricyclic tether dimers (Compounds 102 and 105) were found to be more active than the corresponding 5-membered tether analog, Compound 101 (Table 6). Anti-proliferative activity against the SKBr3 breast cancer cell line was similar for the 6-membered and 7-membered dimers (Compounds 102 and 105), but against MCF-7 cell lines, the 7-membered analog (Compound 103) was 3-fold more active than the 6-membered analog (Compound 102). The tricyclic constrained analogs (Compounds 101-105) were less potent than dimers containing the more flexible biaryl linker (Compounds 65-70). This may indicate that free rotation around the aryl carbon-carbon bond is necessary to orient the methoxy group of the linker and the two coumarin rings into a favorable geometry, since the tricyclic analogs (Compounds 101-105) are conformationally constrained and lack free rotation about these aryl rings.

TABLE 6

Anti-Proliferation Activities of Tricyclic Tether Dimers.

| Entry | n | amide positions | SKBr3 | MCF-7 |
|---|---|---|---|---|
| 101 | 0 | 2,6 | <100[a] | <100 |
| 102 | 1 | 4,8 | 60.1 ± 2.8 | 22.0 ± 3.4 |
| 103 | 1 | 3,8 | <100 | <100 |
| 104 | 1 | 2,8 | <100 | <100 |
| 105 | 2 | 4,10 | 59.9 ± 9.8 | 7.1 ± 1.6 |

[a]Values represent mean ± standard deviation for at least two separate experiments performed in triplicate, all values presented in μM To validate HSP90 as the target responsible for manifesting the observed antiproliferative activities exhibited by these compounds, analogs manifesting $IC_{50}$ values less than 2 µM were evaluated for their ability to induce degradation of HSP90-dependent client proteins (Her-2, Raf, Akt). Since actin is not dependent on HSP90 for its maturation, actin levels should remain constant after treatment with an HSP90 inhibitor and is therefore used as a control.

Figure 12:
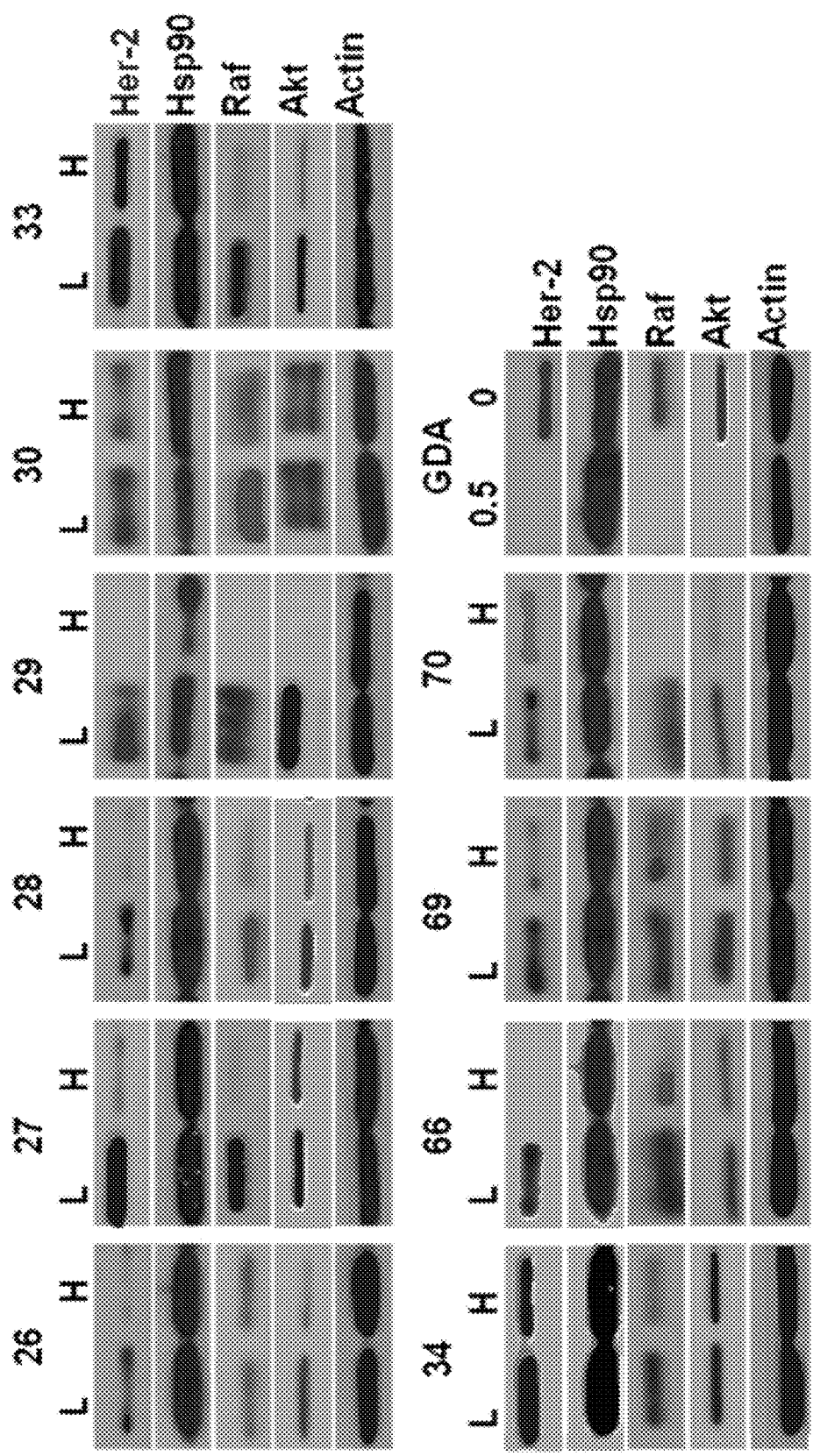
FIG. 12 includes a Western blot analyses of HSP90 client protein degradation in MCF-7 breast cancer cells for coumermycin A1 analogs that target HSP90.

FIG. 12 shows the effect of these compounds on HSP90 client proteins from MCF-7 breast cancer cell lysates following 24 hour treatment with these analogs. Each compound was dosed at two concentrations, H represents a concentration 5-fold higher than the antiproliferative $IC_{50}$ value, whereas L represents a concentration equal to one half of the observed $IC_{50}$ value, while geldanamycin (500 nM, 10× the $IC_{50}$) was used as a positive control and dimethyl sulfoxide as a negative control.

FIG. 12 includes a Western blot analyses of HSP90 client protein degradation in MCF-7 breast cancer cells for coumermycin A1 analogs that target HSP90. L represents a concentration ½ of the anti-proliferative $IC_{50}$ value while H represents a concentration 5 times greater than the anti-proliferative $IC_{50}$ value. GDA (500 nM) represents a positive control, while DMSO (0), vehicle, serves as the negative control.

A majority of the compounds tested by western blot caused the degradation of HSP90 client proteins, while causing no change in actin, which indicates these compounds manifest anti-proliferative activity through HSP90 inhibition. There were 3 compounds (Compounds 31, 32 and 36) that produced unique client protein profiles at the two concentrations tested. Compounds 31 and 36 appeared to manifest no activity against HSP90 client proteins, while Compound 32 only caused degradation of Raf and Akt, but exhibited no effect on Her2. Further studies are needed to determine whether the activity manifested by Compound 27 is dependent upon HSP90. Prior studies have shown that extracellular HSP90, which binds Her2, can be selectively targeted with non-permeable inhibitors.

Figure 13:
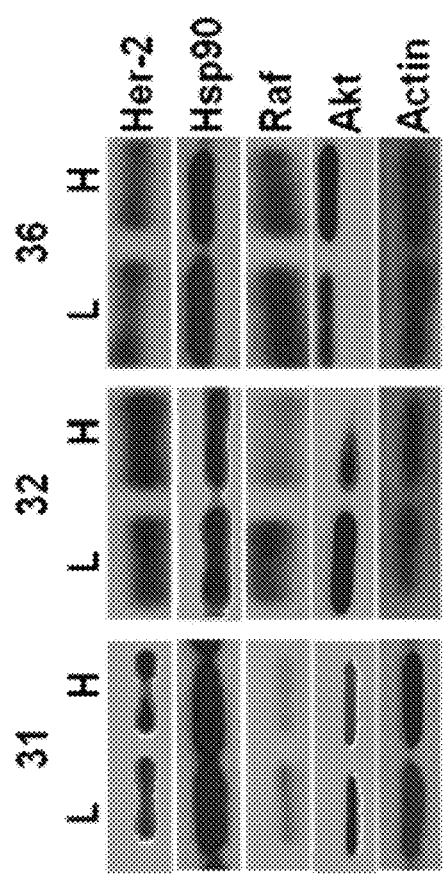
FIG. 13 shows a Western blot analyses of HSP90 client protein degradation in MCF-7 breast cancer cells for coumermycin A1 analogs that appear to not target HSP90.

FIG. 13 shows a Western blot analyses of HSP90 client protein degradation in MCF-7 breast cancer cells for coumermycin A1 analogs that appear to not target HSP90. L represents a concentration ½ of the anti-proliferative $IC_{50}$ value while H represents a concentration 5 times the anti-proliferative $IC_{50}$ value.

In conclusion we have designed and synthesized conformationally constrained coumermycin A1 analogs that were evaluated against both breast cancer (SKBr3 and MCF7) and prostate cancer (PC3mm2, A549 and HT29) cell lines. The first series of analogs included compounds with simplified moieties in lieu of the noviose sugar, while subsequent analogs included varying coumarin, noviose, and tether modifications. Many of these coumermycin A1 analogs manifested potent anti-proliferative activity that correlated directly to HSP90 inhibition as evidenced by the degradation of HSP90-dependent client proteins. Replacement of the laborious, stereochemical complex, and expensive noviose sugar with commercially available piperidine moieties produced compounds that manifested ~100-fold increase in antiproliferative activities.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. An inhibitor of heat shock protein 90 (HSP90), the inhibitor being a coumermycin A1 analog that has a structure of Scaffold 1,

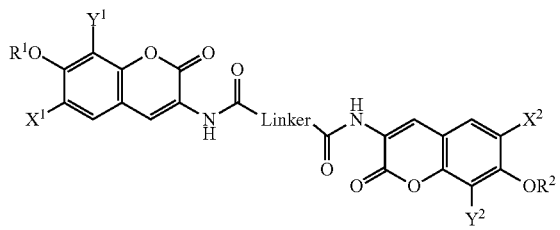

(Scaffold 1)

wherein:
R$^1$ and R$^2$ each independently includes S2 or S3

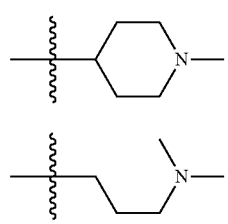

X$^1$, X$^2$, Y$^1$, and Y$^2$ each independently includes a moiety independently selected from hydrogen, halogens, hydroxyls, alkoxys, straight aliphatics, branched aliphatics, cyclic aliphatics, heterocyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, sugars, sugar mimics, or combinations thereof, the aliphatic groups having carbon chains of carbons or hetero atoms or O, N, S, or P; and linker including a straight aliphatic, branched aliphatic, cyclic aliphatic, heterocyclic aliphatic, substituted aliphatic, unsubstituted aliphatic, saturated aliphatic, unsaturated aliphatic, aromatic, polyaromatic, substituted aromatic, hetero-aromatic, amine, primary amine, secondary amine, tertiary amine, aliphatic amine, carbonyl, carboxyl, amide, ester, amino acid, peptide, polypeptide, sugars, sugar mimic, or combinations thereof.

2. The inhibitor of claim 1, wherein X$^1$ or X$^2$ are independently hydrogen or methoxy.

3. The inhibitor of claim 1, wherein Y$^1$ or Y$^2$ are independently methyl or methoxy.

4. The inhibitor of claim 1, wherein linker includes a saturated or unsaturated aliphatic having C$_3$-C$_{10}$, a 1-1'-biphenyl with a methoxy substituent on each phenyl ring, a 6H-benzo[c]chromene compound, 6,7-dihydrodibenzo[b,d]oxepine, or 7,8-dihydro-6H-dibenzo[b,d]oxocine.

5. The inhibitor of claim 1, wherein:
X$^1$ or X$^2$ are independently hydrogen or methoxy;
Y$^1$ or Y$^2$ are independently methyl or methoxy; and
linker includes a saturated or unsaturated aliphatic having C$_3$-C$_{10}$, a 1-1'-biphenyl with a methoxy substituent on each phenyl ring, a 6H-benzo[c]chromene compound, 6,7-dihydrodibenzo[b,d]oxepine, or 7,8-dihydro-6H-dibenzo[b,d]oxocine.

6. The inhibitor of claim 1, wherein linker is L1, L2, or L3, with n for L1 being 0, 1, 2, or 3, and n for L3 being 1, 2, or 3,

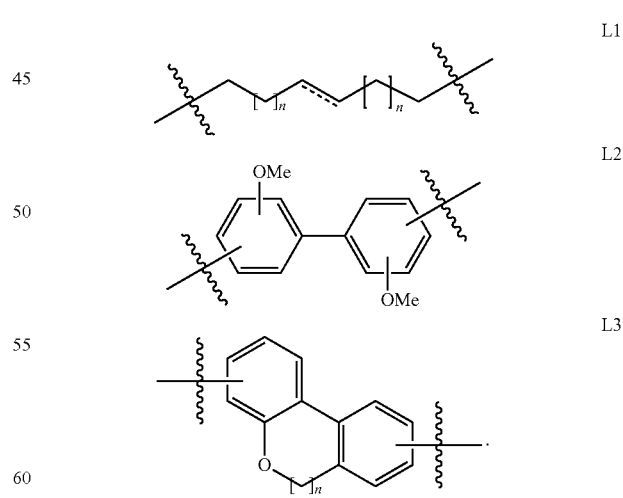

7. The inhibitor of claim 1, wherein the linker is devoid of aryl, heteroaryl or olefin.

8. The inhibitor of claim 1, wherein the coumermycin A1 analog has a structure of Scaffold 2, wherein n and m are independently integers

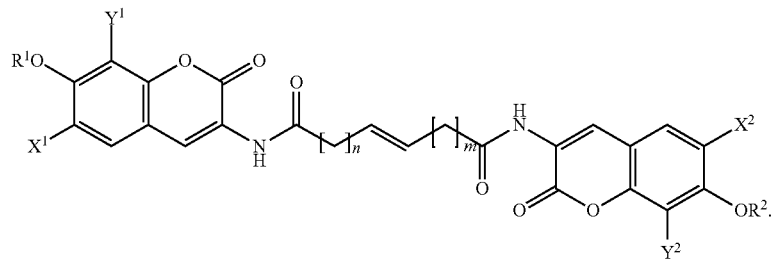
(Scaffold 2)

9. The inhibitor of claim 1, wherein the coumermycin A1 analog has a structure of Scaffold 3, wherein n is an integer

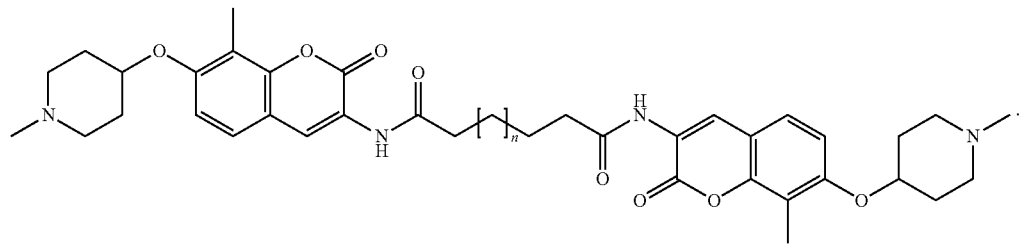
(Scaffold 3)

10. The inhibitor of claim 1, wherein the coumermycin A1 analog is conformationally constrained and has a structure of Scaffold 4,
n1=0, 2,6-dicarboxamide, pseudo-trans;
n1=1, 4,8-dicarboxamide, pseudo-trans;
n1=1, 3,8-dicarboxamide, trans;
n1=1, 2,8-dicarboxamide, pseudo-cis; or
n1=2, 2,6-dicarboxamide, pseudo-trans

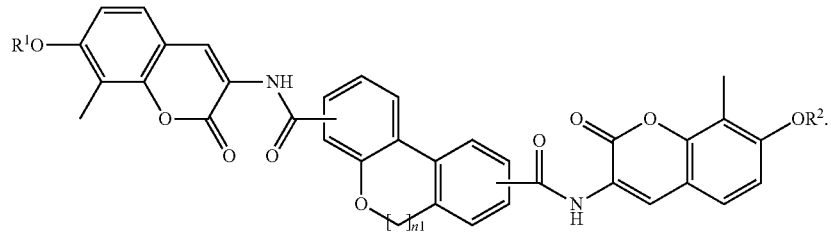
(Scaffold 4)

11. The inhibitor of claim 1, wherein the coumermycin A1 analog has a structure of Scaffold 6, R is $R^1$, X is $X^1$, Y is $Y^1$, and n is 1-4,

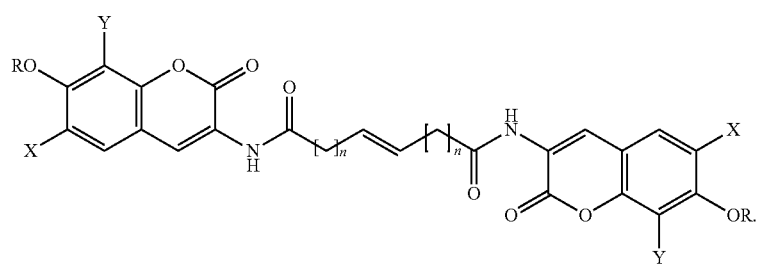
(Scaffold 6)

12. The inhibitor of claim 1, wherein the coumermycin A1 analog has a structure of Scaffold 7, n is 1-5, (Scaffold 7)

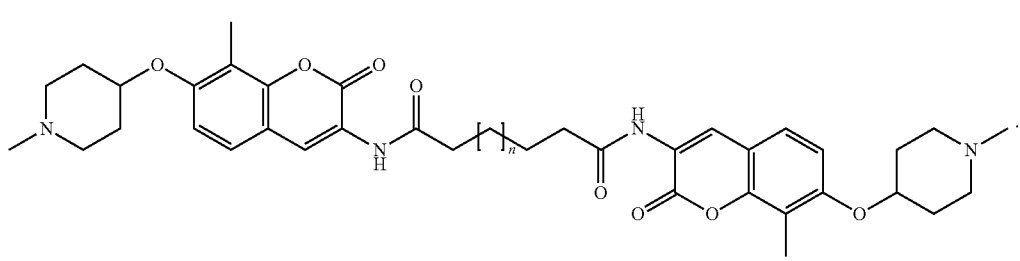

13. The inhibitor of claim 1, wherein the coumermycin A1 analog has a structure of Scaffold 9, $R^3$ is $R^1$, (Scaffold 9)

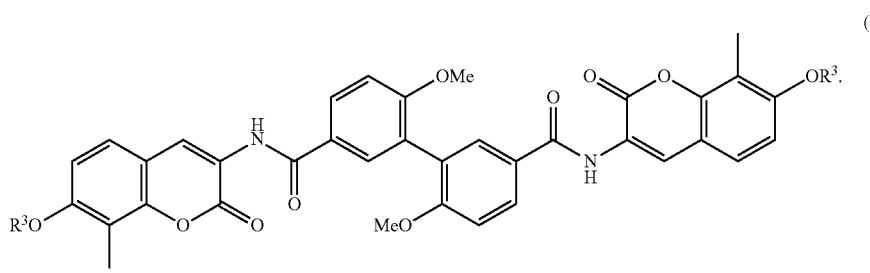

14. A coumermycin A1 analog that has a structure of Scaffold 10, n2 is 1-4, (Scaffold 10)

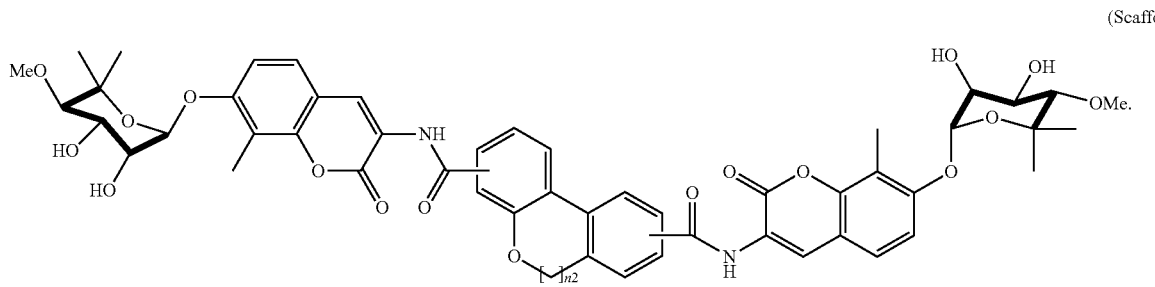

15. A method of inhibiting heat shock protein 90 (HSP90), the method comprising:
   providing a coumermycin A1 analog in accordance with claim 1; and
   contacting the coumermycin A1 analog with a HSP90 so as to inhibit the HSP90.

16. The method of claim 15, wherein the HSP90 is in a cancerous cell.

17. The method of claim 15, wherein the HSP90 is in a patient that has cancer.

18. The method of claim 15, wherein the coumermycin A1 analog has HSP90 inhibiting activity of greater than 10 times the activity of coumermycin A1.

19. The method of claim 15, wherein the coumermycin A1 analog has an anti-proliferative activity of greater than $IC_{50}=70$ µM.

20. A method of degrading a HSP90-dependent client protein, the method comprising:
   providing a coumermycin A1 analog in accordance with claim 2; and
   contacting the coumermycin A1 analog with a HSP90 or HSP90-dependent client protein so as to degrade the client protein.

21. The method of claim 20, wherein the client protein is Her-2, Raf, or Akt.

22. A method of inhibiting cell proliferation, the method comprising:
   providing a coumermycin A1 analog in accordance with claim 2; and
   contacting the coumermycin A1 analog with a potentially proliferative cell in a sufficient amount to inhibit proliferation of the cell.

23. The inhibitor of claim 11, wherein:
   X is selected from the group consisting of hydrogen, methyl, methoxy,
   Y is selected from the group consisting of methyl and methoxy,
   n is selected from 1, 2, 3, or 4.

24. The inhibitor of claim 23, wherein the coumermycin A1 analog includes one of compounds 26-36 or 38 having R, n, X, and Y defined as follows:

| Compound # | R | n | X | Y |
|---|---|---|---|---|
| 26 | piperidine-N-methyl | 1 | H | Me |
| 29 | piperidine-N-methyl | 2 | H | Me |
| 32 | piperidine-N-methyl | 3 | H | Me |
| 35 | piperidine-N-methyl | 4 | H | Me |
| 27 | piperidine-N-methyl | 1 | OMe | Me |
| 30 | piperidine-N-methyl | 2 | OMe | Me |
| 33 | piperidine-N-methyl | 3 | OMe | Me |
| 28 | piperidine-N-methyl | 1 | H | OMe |
| 31 | piperidine-N-methyl | 2 | H | OMe |
| 34 | piperidine-N-methyl | 3 | H | OMe |
| 36 | N,N-dimethylaminoethyl | 1 | H | Me |
| 38 | piperidine-N-methyl (cis-isomer) | 2 | H | Me. |

25. The inhibitor of claim 12, wherein n is 1, 3, or 5.

26. An inhibitor of heat shock protein 90 (HSP90), the inhibitor being a coumermycin A1 analog that has a structure of Scaffold 1,

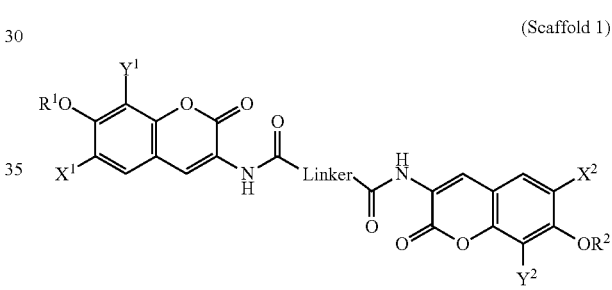

(Scaffold 1)

wherein:
$R^1$, $R^2$, $X^1$, $X^2$, $Y^1$, and $Y^2$ each independently includes a moiety independently selected from hydrogen, halogens, hydroxyls, alkoxys, straight aliphatics, branched aliphatics, cyclic aliphatics, heterocyclic aliphatics, substituted aliphatics, unsubstituted aliphatics, saturated aliphatics, unsaturated aliphatics, aromatics, polyaromatics, substituted aromatics, heteroaromatics, amines, primary amines, secondary amines, tertiary amines, aliphatic amines, carbonyls, carboxyls, amides, esters, amino acids, peptides, polypeptides, sugars, sugar mimics, or combinations thereof, the aliphatic groups having carbon chains of carbons or hetero atoms or O, N, S, or P; provided that $R_1$ and $R_2$ are not a noviose sugar moiety; and linker is L1, L2, or L3, with n for L1 being 0, 1, 2, or 3, and n for L3 being 1, 2, or 3,

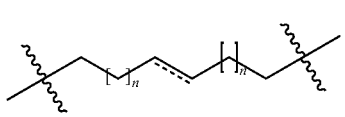

L1

-continued
L2
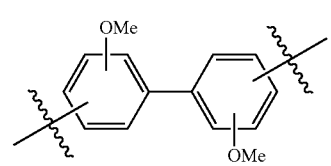
L3
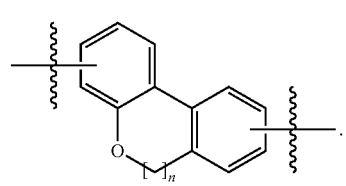
27. The inhibitor of claim 26, wherein $R^1$ and $R^2$ are independently S2 or S3,
S2
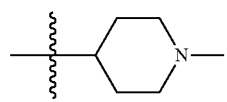
S3
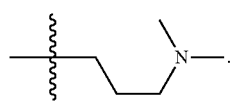
* * * * *

UNITED STATES PATENT AND TRADEMARK OFFICE
CERTIFICATE OF CORRECTION

PATENT NO. : 9,056,104 B2  
APPLICATION NO. : 13/473046  
DATED : June 16, 2015  
INVENTOR(S) : Brian S. J. Blagg and Bhaskar Reddy Kusuma Page 1 of 1

It is certified that error appears in the above-identified patent and that said Letters Patent is hereby corrected as shown below:

In the claims

In claim 20, column 35, line 7, delete "2" and insert --1-- therefor.

In claim 22, column 35, line 16, delete "2" and insert --1-- therefor.

In claim 23, column 35, line 22, delete ", methyl," and insert --and-- therefor.

Signed and Sealed this
Twentieth Day of October, 2015

Michelle K. Lee
*Director of the United States Patent and Trademark Office*